US012728265B2

(12) United States Patent
Krishnamoorthi

(10) Patent No.: US 12,728,265 B2
(45) Date of Patent: Sep. 8, 2026

(54) BINAURAL LOUDNESS CUE PRESERVATION IN BIMODAL HEARING SYSTEMS

(71) Applicant: Cochlear Limited, Macquarie University (AU)

(72) Inventor: Harish Krishnamoorthi, Englewood, CO (US)

(73) Assignee: Cochlear Limited, Macquarie University (AU)

( * ) Notice: Subject to any disclaimer, the term of this patent is extended or adjusted under 35 U.S.C. 154(b) by 526 days.

(21) Appl. No.: 18/005,091

(22) PCT Filed: Jun. 7, 2021

(86) PCT No.: PCT/IB2021/054973
§ 371 (c)(1),
(2) Date: Jan. 11, 2023

(87) PCT Pub. No.: WO2022/013639
PCT Pub. Date: Jan. 20, 2022

(65) Prior Publication Data

US 2023/0338733 A1 Oct. 26, 2023

Related U.S. Application Data

(60) Provisional application No. 63/052,004, filed on Jul. 15, 2020.

(51) Int. Cl.

| | |
|---|---|
| ***A61N 1/36*** | (2006.01) |
| ***A61N 1/05*** | (2006.01) |
| ***H04R 25/00*** | (2006.01) |

(52) U.S. Cl.
CPC ....... *A61N 1/36038* (2017.08); *A61N 1/0541* (2013.01); *H04R 25/50* (2013.01); *H04R 25/606* (2013.01); *H04R 2225/67* (2013.01)

(58) Field of Classification Search
CPC .............. A61N 1/36038; A61N 1/0541; A61N 1/0456; A61N 1/36125; H04R 25/50; H04R 25/606; H04R 2225/67
See application file for complete search history.

(56) References Cited

U.S. PATENT DOCUMENTS

| | | | |
|---|---|---|---|
| 4,289,935 | A | 9/1981 | Zollner et al. |
| 5,870,481 | A | 2/1999 | Dymond et al. |

(Continued)

FOREIGN PATENT DOCUMENTS

| | | | |
|---|---|---|---|
| CN | 104685907 | A | 6/2015 |
| CN | 109997374 | A | 7/2019 |

(Continued)

OTHER PUBLICATIONS

Vroegop et. al., "Comparing the Effect of Different Hearing Aid Fitting Methods in Bimodal Cochlear Implant Users", Mar. 2019, American Journal of Audiology, vol. 28, pp. 1-10 (Year: 2019).*

(Continued)

*Primary Examiner* — Catherine M Voorhees
(74) *Attorney, Agent, or Firm* — Edell, Shapiro & Finnan, LLC

(57) ABSTRACT

Presented herein are techniques to calculate long-term loudness measures for each of the prostheses in a bimodal hearing system and exchange this information across the two sides. The bimodal hearing system operates to ensure that the loudness differences between the two sides follow the ILDs between the two sides. Stated differently, the techniques presented herein determine a target loudness ratio based on the input signals (sound signals) received at each of the first second hearing prostheses in a bimodal hearing system. The techniques presented herein further determine an estimated inter-aural loudness ratio based on output signals that would be generated by each of the first and second hearing prostheses based on the input signals. Opera- (Continued)

272

100 101 102 106 150 141R 141L

RECEIVE INPUT SIGNALS AT FIRST AND SECOND HEARING PROSTHESES OF A BIMODAL HEARING SYSTEM — 274

DETERMINE A TARGET LOUDNESS RATIO BASED ON A LOUDNESS OF INPUT SIGNALS RECEIVED AT THE FIRST AND SECOND HEARING PROSTHESES — 276

DETERMINE AN INTRA-AURAL LOUDNESS RATION BASED ON AN ESTIMATED LOUDNESS OF OUTPUT SIGNALS OF THE FIRST AND SECOND HEARING PROSTHESES — 278

DETERMINE ONE OR MORE ADJUSTMENTS TO OPERATION OF ONE OR MORE OF THE FIRST OR SECOND HEARING PROSTHESES SO AS TO MATCH THE INSTANTANEOUS LOUDNESS RATIO TO THE TARGET LOUDNESS RATIO — 280 tion of either or both of the first or second hearing prostheses is adjusted so as to substantially match the estimated inter-aural loudness ratio to the target loudness ratio.

18 Claims, 12 Drawing Sheets

(56) References Cited

U.S. PATENT DOCUMENTS 7,171,272 B2 * 1/2007 Blamey .............. A61N 1/36038 607/57
8,503,704 B2 8/2013 Francart et al.
8,571,674 B2 10/2013 Nicolai et al.
8,712,063 B2 4/2014 Roeck et al.
8,953,810 B2 2/2015 Meskens et al.
8,953,819 B2 2/2015 Ko et al.
9,491,559 B2 11/2016 Anderson
9,592,381 B2 3/2017 Kulkarni
9,775,999 B2 10/2017 Chalupper
9,866,976 B2 * 1/2018 Riis ........................ H04R 25/70
9,973,865 B2 5/2018 Francart et al.
10,091,592 B2 10/2018 Chen et al.
10,149,072 B2 12/2018 Long et al.
10,194,814 B2 * 2/2019 Fung .................... H04R 25/505
2006/0287690 A1 12/2006 Bouchataoui et al.
2015/0215710 A1 * 7/2015 Francart ................. H04R 25/70 381/326
2016/0330551 A1 11/2016 Brown
2018/0091907 A1 * 3/2018 Long .................... H04R 25/552
2019/0364370 A1 11/2019 Riis et al.
2020/0077212 A1 3/2020 Hamacher et al.

FOREIGN PATENT DOCUMENTS

CN 110520188 A 11/2019
EP 2974378 B1 4/2018
JP 2004-506398 A 2/2004
WO 2018171858 A1 9/2018

OTHER PUBLICATIONS

International Search Report and Written Opinion in counterpart International Application No. PCT/IB2021/054973, mailed Sep. 8, 2021, 9 pages.
Maaike Van Eeckhoutte et al., "Objective Binaural Loudness Balancing Based on 40-Hz Auditory Steady-State Responses. Part II: Asymmetric and Bimodal Hearing", Trends in Hearing vol. 22: 1-14, DOI:10.1177/2331216518805363, Nov. 30, 2017, 14 pages.
Jantien L. Vroegop et al., "Comparing the Effect of Different Hearing Aid Fitting Methods in Bimodal Cochlear Implant Users", American Journal of Audiology, vol. 28, 1-10, Mar. 2019, 11 pages.

* cited by examiner 148
152
BTE SOUND
PROCESSING UNIT
150
HEARING
AID
ITE
RECEIVER
154
112
IMPLANTABLE
COMPONENT
100
114
116
142
106
102
COCHLEAR
IMPLANT
104
EXTERNAL
COMPONENT COCHLEAR IMPLANT
102
EXTERNAL COMPONENT
104
SOUND PROCESSING UNIT
106
SKIN/TISSUE
115
IMPLANTABLE COIL
114
108
122
RF TRANSCEIVER
POWER SOURCE
123
118
SOUND INPUT DEVICE(S)
119
AUXILIARY INPUT DEVICE(S)
120
WIRELESS TRANSCEIVER
124
125
PROCESSOR(S)
126
MEMORY
128
BIMODAL SOUND PROCESSING LOGIC
138
140
RF INTERFACE CIRCUITRY
N
142
STIMULATOR UNIT
134
136
116
144
146
112
IMPLANTABLE COMPONENT 153
SOUND PROCESSING UNIT 152
158
SOUND INPUT DEVICE(S)
AUXILIARY INPUT DEVICE(S)
159
WIRELESS TRANSCEIVER
160
166
168
BIMODAL SOUND PROCESSING LOGIC
164
165
PROCESSOR(S)
MEMORY
163
POWER SOURCE
171
HEARING AID 150
EAR MOLD 169
154 ITE COMPONENT
170 ACOUSTIC RECEIVER 150 HEARING AID
593
GAIN
594
GAIN DETERMINATION UNIT
170
$L^O_{HA}$
$TLR_{HA}$
$L^O_{CI}$
591
591
ACOUSTIC LOUDNESS ESTIMATION
592
596
TARGET LOUDNESS RATIO DETERMINATION
590
HA PROCESSING
ILD OR $L^I_{CI}$
MASTER CONTROL
598
$X_{HA}$
589

102 COCHLEAR IMPLANT
693
GAIN
112
TO ELECTRODES
694
GAIN DETERMINATION UNIT
691
691
ELECTRIC LOUDNESS ESTIMATION
692
$L^{O}_{CI}$
$TLR_{CI}$
$L^{O}_{HA}$
$TLR_{CI}$
696
TARGET LOUDNESS RATIO DETERMINATION
690
CI PROCESSING
ILD OR $L^{I}_{HA}$
MASTER CONTROL
698
$X_{CI}$
689

HEARING AID
597
ACOUSTIC LOUDNESS MODEL
589
$X_{HA}$
$L^{I}_{HA}$
596
TARGET LOUDNESS RATIO
$TLR_{CI}=L^{I}_{HA}/L^{I}_{CI}$
$L^{I}_{HA}$
$L^{I}_{CI}$
$TLR_{HA}$
598
MASTER CONTROL
COCHLEAR IMPLANT
697
ACOUSTIC LOUDNESS MODEL
689
$X_{CI}$
$L^{I}_{CI}$
696
TARGET LOUDNESS RATIO
$TLR_{CI}=L^{I}_{CI}/L^{I}_{HA}$
$L^{I}_{CI}$
$L^{I}_{HA}$
$TLR_{CI}$
698
MASTER CONTROL

Figure 9:
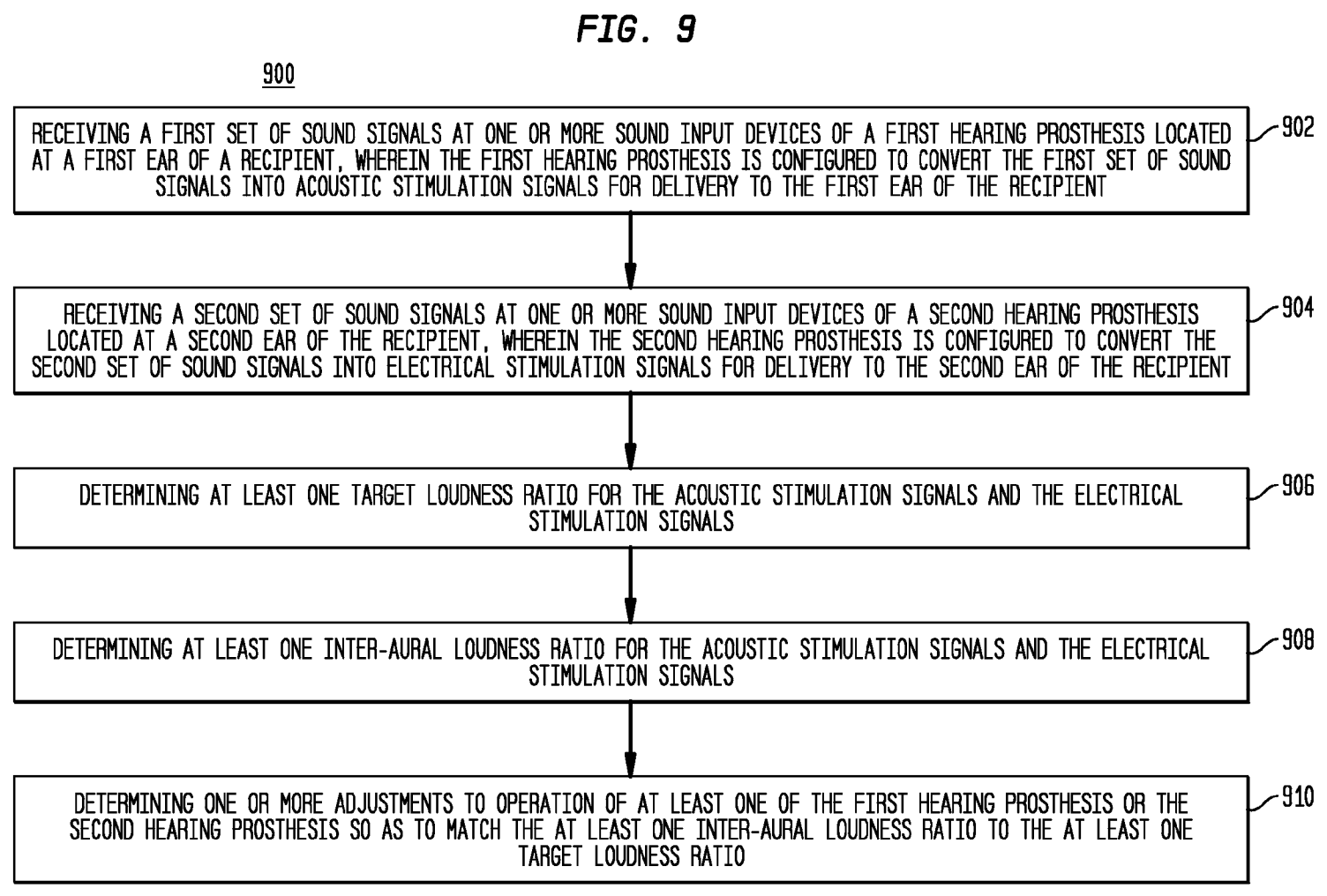

RECEIVING A FIRST SET OF SOUND SIGNALS AT ONE OR MORE SOUND INPUT DEVICES OF A FIRST HEARING PROSTHESIS LOCATED AT A FIRST EAR OF A RECIPIENT, WHEREIN THE FIRST HEARING PROSTHESIS IS CONFIGURED TO CONVERT THE FIRST SET OF SOUND SIGNALS INTO ACOUSTIC STIMULATION SIGNALS FOR DELIVERY TO THE FIRST EAR OF THE RECIPIENT — 902

RECEIVING A SECOND SET OF SOUND SIGNALS AT ONE OR MORE SOUND INPUT DEVICES OF A SECOND HEARING PROSTHESIS LOCATED AT A SECOND EAR OF THE RECIPIENT, WHEREIN THE SECOND HEARING PROSTHESIS IS CONFIGURED TO CONVERT THE SECOND SET OF SOUND SIGNALS INTO ELECTRICAL STIMULATION SIGNALS FOR DELIVERY TO THE SECOND EAR OF THE RECIPIENT — 904

DETERMINING AT LEAST ONE TARGET LOUDNESS RATIO FOR THE ACOUSTIC STIMULATION SIGNALS AND THE ELECTRICAL STIMULATION SIGNALS — 906

DETERMINING AT LEAST ONE INTER-AURAL LOUDNESS RATIO FOR THE ACOUSTIC STIMULATION SIGNALS AND THE ELECTRICAL STIMULATION SIGNALS — 908

DETERMINING ONE OR MORE ADJUSTMENTS TO OPERATION OF AT LEAST ONE OF THE FIRST HEARING PROSTHESIS OR THE SECOND HEARING PROSTHESIS SO AS TO MATCH THE AT LEAST ONE INTER-AURAL LOUDNESS RATIO TO THE AT LEAST ONE TARGET LOUDNESS RATIO — 910

BINAURAL LOUDNESS CUE PRESERVATION IN BIMODAL HEARING SYSTEMS

BACKGROUND

Field of the Invention

The present invention relates generally to the preservation of binaural loudness cues in bimodal hearing systems.

Related Art

Medical devices have provided a wide range of therapeutic benefits to recipients over recent decades. Medical devices can include internal or implantable components/devices, external or wearable components/devices, or combinations thereof (e.g., a device having an external component communicating with an implantable component). Medical devices, such as traditional hearing aids, partially or fully-implantable hearing prostheses (e.g., bone conduction devices, mechanical stimulators, cochlear implants, etc.), pacemakers, defibrillators, functional electrical stimulation devices, and other medical devices, have been successful in performing lifesaving and/or lifestyle enhancement functions and/or recipient monitoring for a number of years.

The types of medical devices and the ranges of functions performed thereby have increased over the years. For example, many medical devices, sometimes referred to as "implantable medical devices," now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, implantable components.

SUMMARY

In one aspect presented herein, a method is provided. The method comprises: receiving a first set of sound signals at one or more sound input devices of a first hearing prosthesis located at a first ear of a recipient, wherein the first hearing prosthesis is configured to convert the first set of sound signals into acoustic stimulation signals for delivery to the first ear of the recipient; receiving a second set of sound signals at one or more sound input devices of a second hearing prosthesis located at a second ear of the recipient, wherein the second hearing prosthesis is configured to convert the second set of sound signals into electrical stimulation signals for delivery to the second ear of the recipient; determining at least one target loudness ratio for the acoustic stimulation signals and the electrical stimulation signals; determining at least one inter-aural loudness ratio for the acoustic stimulation signals and the electrical stimulation signals; and determining one or more adjustments to operation of at least one of the first hearing prosthesis or the second hearing prosthesis so as to match the at least one inter-aural loudness ratio to the at least one target loudness ratio.

In another aspect presented herein, one or more non-transitory computer readable storage media are provided. The one or more non-transitory computer readable storage media comprise instructions that, when executed by at least one processor, are operable to: calculate a target loudness ratio based on a loudness of input signals received at each of a first hearing prosthesis and a second hearing prosthesis of a bimodal hearing system; calculate an instantaneous loudness ratio based on a loudness of output signals generated at each of the first hearing prosthesis and the second hearing prosthesis; and set a gain used to generate output signals at either the first hearing prosthesis or the second hearing prosthesis such that the instantaneous loudness ratio is within a predetermined range of the target loudness ratio.

In another aspect presented herein, a first hearing prosthesis configured to operate with a second hearing prosthesis in a bimodal hearing system is provided. The first hearing prosthesis comprises: one or more sound input devices configured to receive a first set of sound signals; and one or more processors configured to: convert the first set of sound signals into stimulation signals for delivery to a first ear of a recipient, calculate a target loudness ratio based on a loudness of the first set of sound signals and a loudness of a second set of sound signals received at the second hearing prosthesis, calculate an inter-aural loudness ratio based on a loudness of the stimulation signals for delivery to a first ear of the recipient and a loudness of stimulation signals generated by the second hearing prosthesis for delivery to a second ear of the recipient, and determine an adjusted gain setting for use in generating subsequent stimulation signals for delivery to the first ear of the recipient that will cause the inter-aural loudness ratio to substantially match the target loudness ratio.

BRIEF DESCRIPTION OF THE DRAWINGS

Embodiments of the present invention are described herein in conjunction with the accompanying drawings, in which:

FIG. TA is a schematic view of a bimodal hearing system in which embodiments presented herein may be implemented;

FIG. 9 is a flowchart of an example method, in accordance with certain embodiments presented herein.

DETAILED DESCRIPTION

Figures 1A, 1B:
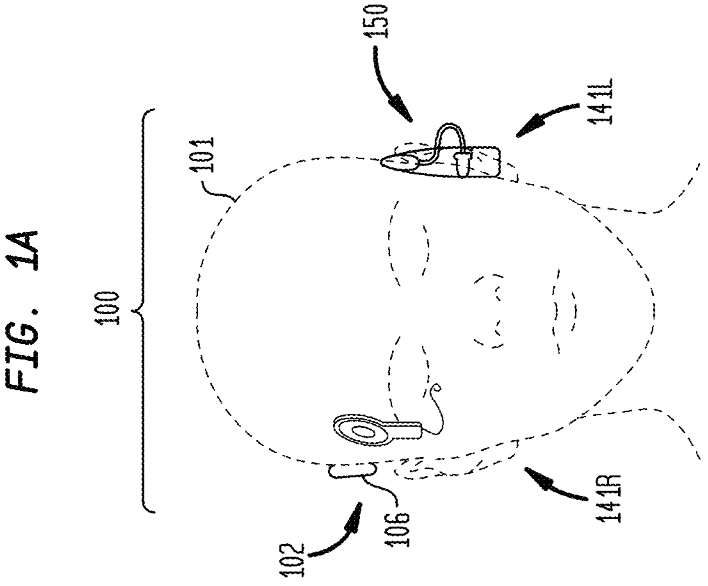
FIG. 1B is a side view of a recipient wearing the bimodal hearing system of FIG. TA.

Medical devices and medical device systems (e.g., including multiple implantable medical devices) have provided a wide range of therapeutic benefits to recipients over recent decades. For example, a hearing prosthesis system (hearing system) is a type of implantable medical device system that includes one or more hearing prostheses that operate to convert sound signals into one or more of acoustic, mechanical, and/or electrical stimulation signals for delivery to a recipient. The one or more hearing prostheses that can form part of a hearing system include, for example, hearing aids, cochlear implants, middle ear stimulators, bone conduction devices, brain stem implants, electro-acoustic cochlear implants or electro-acoustic devices, and other devices providing acoustic, mechanical, and/or electrical stimulation to a recipient.

One specific type of hearing prosthesis system, referred to herein as a "binaural hearing prosthesis system" or more simply as a "binaural hearing system," includes two hearing prostheses, where one of the two hearing prosthesis is positioned at each ear of the recipient. In a binaural system, each of the two prostheses provides stimulation to one of the two ears of the recipient (i.e., either the right or the left ear of the recipient).

Binaural hearing systems can generally be classified as either a "bilateral" hearing system or a "bimodal" hearing system. A bilateral hearing system is a system in which the two hearing prostheses provide the same type/mode of stimulation to a recipient. For example, a bilateral hearing system can comprise two cochlear implants, two hearing aids, two bone conduction devices, etc. In contrast, a bimodal hearing system is a system in which the two hearing prostheses provide different types/modes of stimulation to each ear of the recipient. For example, a bimodal system can comprise a cochlear implant at a first ear of the recipient and a hearing aid at the second ear of recipient, a cochlear implant at a first ear of the recipient and a bone conduction device at a second ear of the recipient, etc.

In normal hearing, the main binaural cues for left/right sound localization are the Interaural (Inter-aural) Level Difference (ILD) and the Interaural (Inter-aural) Time Difference (ITD). A primary benefit of a bilateral hearing system, such as a bilateral cochlear implant system (e.g., two cochlear implants), is that such systems can provide a recipient with ILD (inter-aural level difference) cues. That is, due to the use of similar signal processing techniques at both prosthesis, bilateral hearing systems can reliably map ILD measures to loudness differences across the two ears. However, since bimodal hearing systems are comprised of two different types of hearing prostheses with different types of output stimulation (output signals) and, accordingly different types of signal processing, conventional bimodal hearing systems cannot map ILD measures to loudness differences in a reliable manner. As such, in conventional bimodal systems, even without any head-shadow, there are loudness mismatches across the two ears. With head-shadow, the loudness differences across the two ears becomes even more inconsistent (e.g., better in certain situations, worse in other situations, but overall inconsistent).

As such, presented herein are techniques to calculate long-term loudness measures for each of the prostheses in a bimodal hearing system and exchange this information across the two sides. The bimodal hearing system operates to ensure that the loudness differences between the two sides follow the ILDs between the two sides. Stated differently, the techniques presented herein determine a target loudness ratio based on the input signals (sound signals) received at each of the first and second hearing prostheses in a bimodal hearing system. The techniques presented herein further determine an estimated inter-aural loudness ratio based on output signals that would be generated by each of the first and second hearing prostheses based on the input signals. Operation of either or both of the first or second hearing prostheses is adjusted so as to substantially match/align the estimated inter-aural loudness ratio with the target loudness ratio.

Merely for ease of description, the techniques presented herein are primarily described herein with reference to a specific medical device system, namely a bimodal hearing system comprising a cochlear implant and a hearing aid. However, it is to be appreciated that the techniques presented herein may also be used with a variety of other implantable medical device systems. For example, the techniques presented herein may be used with other hearing systems, including combinations of any of a cochlear implant, middle ear auditory prosthesis (middle ear implant), bone conduction device, direct acoustic stimulator, electro-acoustic prosthesis, auditory brain stimulator systems, etc. The techniques presented herein may also be used with systems that comprise or include tinnitus therapy devices, vestibular devices (e.g., vestibular implants), visual devices (i.e., bionic eyes), sensors, pacemakers, drug delivery systems, defibrillators, functional electrical stimulation devices, catheters, seizure devices (e.g., devices for monitoring and/or treating epileptic events), sleep apnea devices, electroporation devices, etc.

Figure 1C:
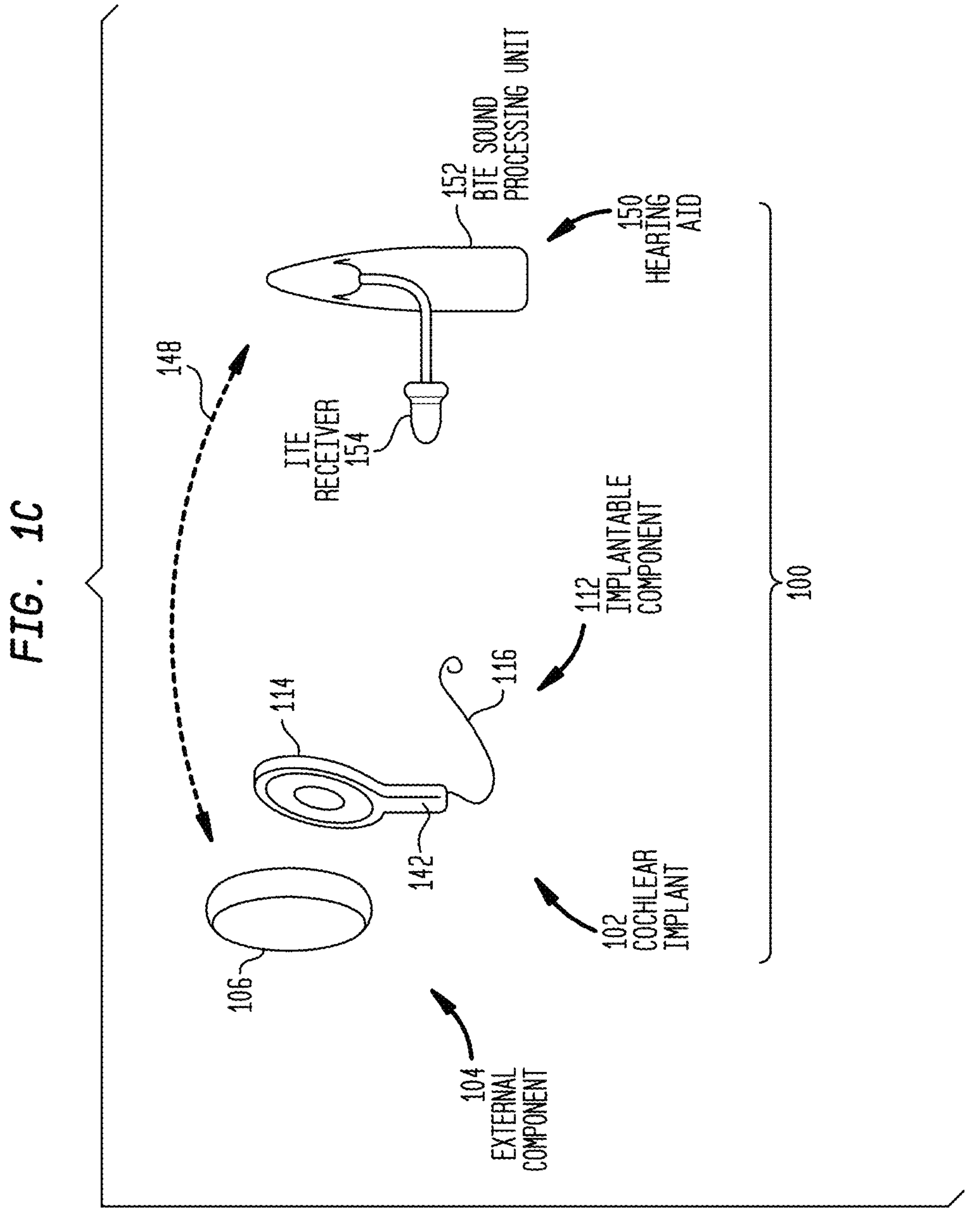
FIG. 1C is a schematic view of the components of the bimodal hearing system of FIG. 1A.

FIGS. 1A-1E are diagrams illustrating one example bimodal hearing system 100 configured to implement the techniques presented herein. As shown in FIGS. 1A and 1B, the bimodal hearing system 100 comprises a cochlear implant 102 and a hearing aid 115. FIGS. 1A and 1B are schematic drawings of a recipient wearing the cochlear implant 102 at a right ear 141R of the recipient and wearing the hearing aid 150 at a left ear 141L of the recipient, while FIG. 1C is a schematic diagram illustrating each of the cochlear implant 102 and the hearing aid 150 separate from the head 101 of the recipient.

As shown in FIG. 1C, the cochlear implant 102 includes an external component 104 that is configured to be directly or indirectly attached to the body of the recipient and an implantable component 112 configured to be implanted in the head 101 of recipient. The external component 104 comprises a sound processing unit 106, while the implantable component 112 includes an internal coil 114, a stimulator unit 142 and an elongate stimulating assembly (electrode array) 116 implanted in the recipient's left cochlea (not shown in FIG. 1C). Hearing aid 150 comprises a sound processing unit 152 and an in-the-ear (ITE) component 154.

In the embodiment of FIGS. 1A-1E, the hearing aid 150 (e.g., sound processing unit 152) and the cochlear implant 102 (e.g., sound processing unit 106) communicate with one another over a wired or wireless communication channel/link 148. The communication channel 148 is a bidirectional communication channel and may be, for example, a magnetic inductive (MI) link, a short-range wireless link, such as a Bluetooth® link that communicates using short-wavelength Ultra High Frequency (UHF) radio waves in the industrial, scientific and medical (ISM) band from 2.4 to 2.485 gigahertz (GHz), or another type of wireless link. Bluetooth® is a registered trademark owned by the Bluetooth® SIG.

Figure 1D:
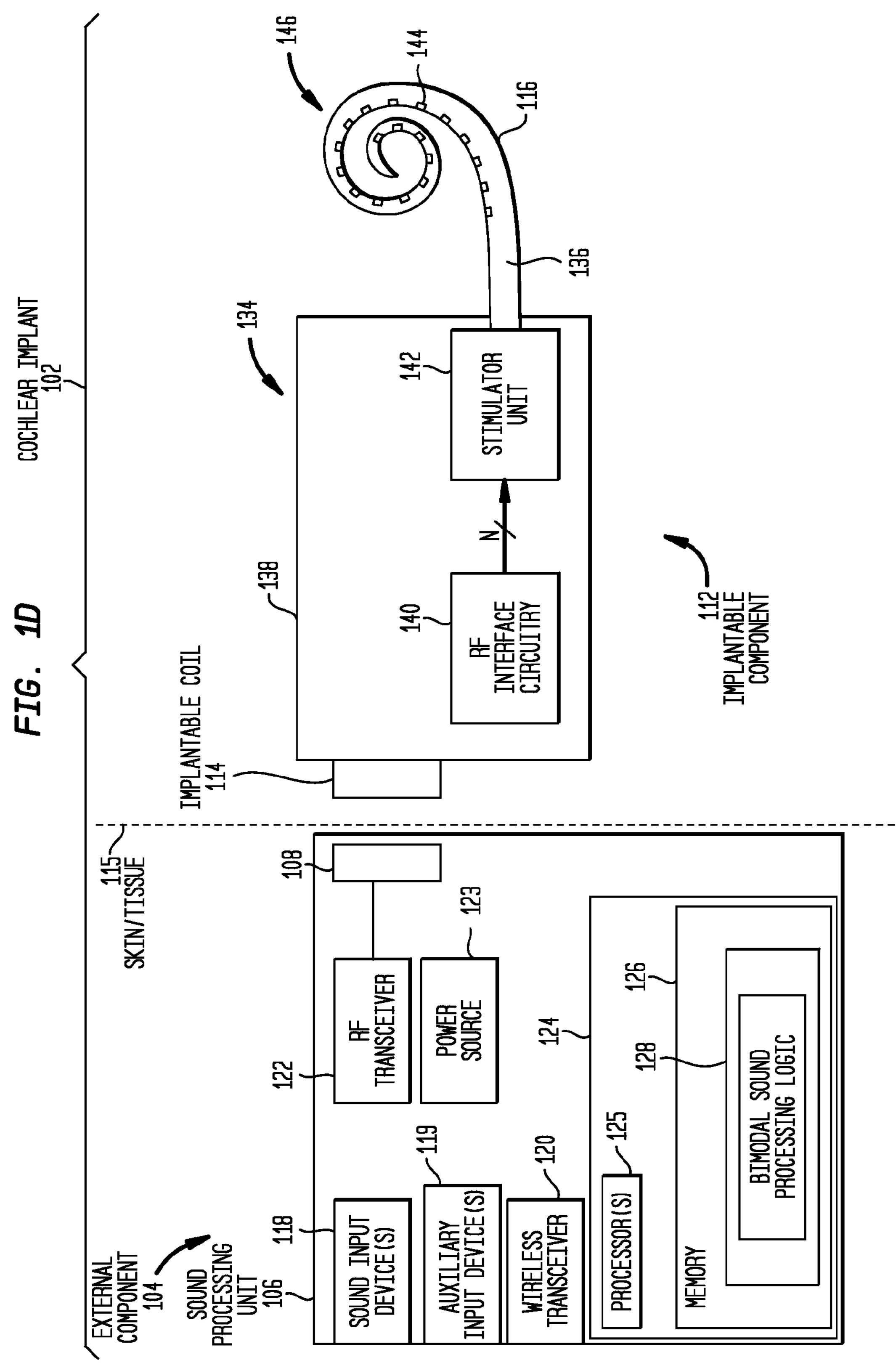
FIG. 1D is a block diagram of a cochlear implant forming part of the bimodal hearing system of FIG. 1A.
Figure 1E:
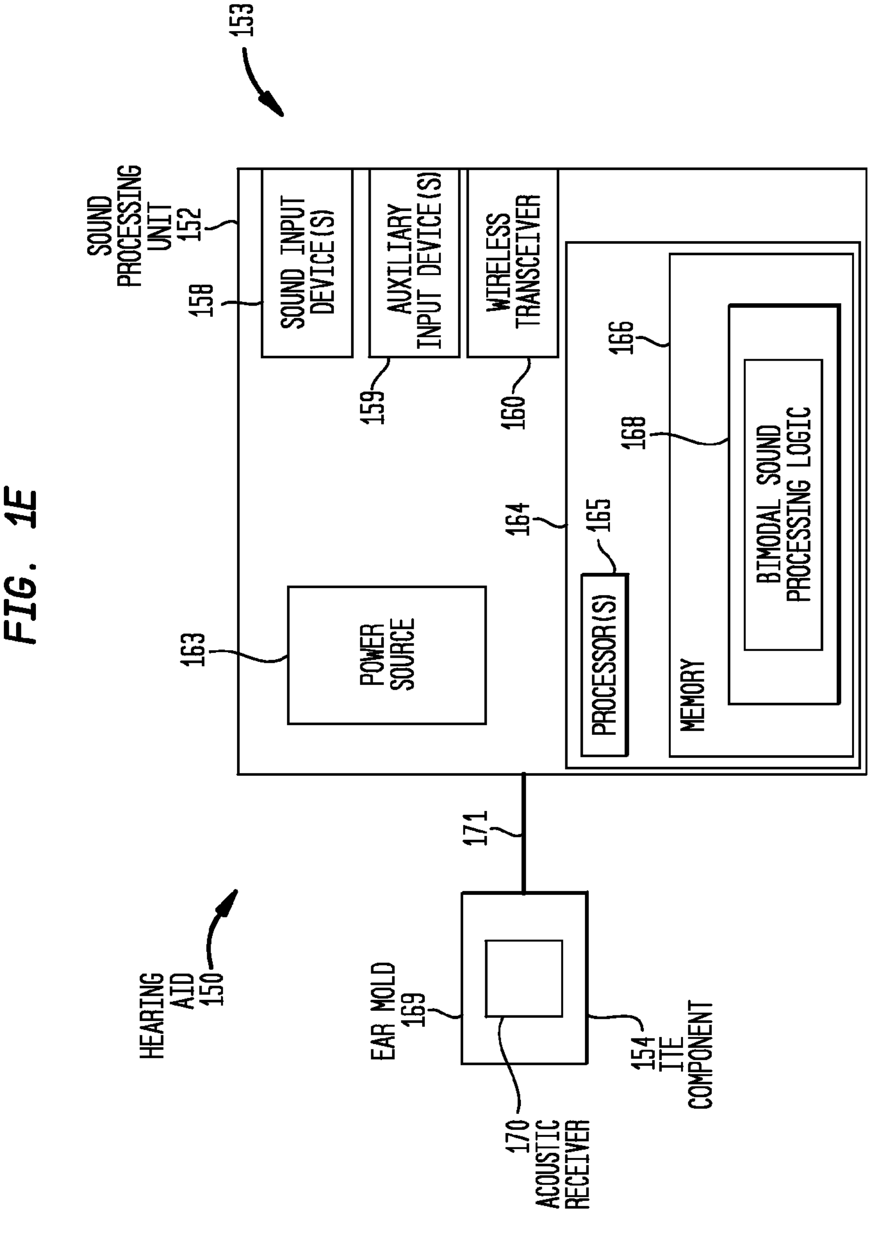
FIG. 1E is a block diagram of a hearing aid forming part of the bimodal hearing system of FIG. 1A.

FIG. 1D is a block diagram illustrating further details of cochlear implant 102, while FIG. 1E is a block diagram illustrating further details of hearing aid 150. As noted, the external component 104 of cochlear implant 102 includes a sound processing unit 106. The sound processing unit 106 comprises one or more input devices 113 that are configured to receive input signals (e.g., sound or data signals). In the example of FIG. 1D, the one or more input devices 113 include one or more sound input devices 118 (e.g., microphones, audio input ports, telecoils, etc.), one or more auxiliary input devices 119 (e.g., audio ports, such as a Direct Audio Input (DAI), data ports, such as a Universal Serial Bus (USB) port, cable port, etc.), and a wireless transmitter/receiver (transceiver) 120. However, it is to be appreciated that one or more input devices 113 may include additional types of input devices and/or less input devices (e.g., the wireless transceiver 120 and/or one or more auxiliary input devices 119 could be omitted).

The sound processing unit 106 also comprises a closely-coupled transmitter/receiver (transceiver) 122, referred to as or radio-frequency (RF) transceiver 122, a power source 123, and a processing module 124. The processing module 124 comprises one or more processors 125 and a memory 126 that includes bimodal sound processing logic 128. In the examples of FIGS. 1A-1E, the sound processing unit 106 is an off-the-ear (OTE) sound processing unit (i.e., a component having a generally cylindrical shape and which is configured to be magnetically coupled to the recipient's head). However, it is to be appreciated that embodiments of the techniques presented herein may be implemented by sound processing units having other arrangements, such as by a behind-the-ear (BTE) sound processing unit configured to be attached to and worn adjacent to the recipient's ear, including a mini or micro-BTE unit, an in-the-canal unit that is configured to be located in the recipient's ear canal, a body-worn sound processing unit, etc.

The implantable component 112 comprises an implant body (main module) 134, a lead region 136, and the intra-cochlear stimulating assembly 116, all configured to be implanted under the skin/tissue (tissue) 115 of the recipient. The implant body 134 generally comprises a hermetically-sealed housing 138 in which RF interface circuitry 140 and a stimulator unit 142 are disposed. The implant body 134 also includes the internal/implantable coil 114 that is generally external to the housing 138, but which is connected to the transceiver 140 via a hermetic feedthrough (not shown in FIG. 1D).

As noted, stimulating assembly 116 is configured to be at least partially implanted in the recipient's cochlea. Stimulating assembly 116 includes a plurality of longitudinally spaced intra-cochlear electrical stimulating contacts (electrodes) 144 that collectively form a contact or electrode array 146 for delivery of electrical stimulation (current) to the recipient's cochlea.

Stimulating assembly 116 extends through an opening in the recipient's cochlea (e.g., cochleostomy, the round window, etc.) and has a proximal end connected to stimulator unit 142 via lead region 136 and a hermetic feedthrough (not shown in FIG. 1D). Lead region 136 includes a plurality of conductors (wires) that electrically couple the electrodes 144 to the stimulator unit 142.

As noted, the cochlear implant 102 includes the external coil 108 and the implantable coil 114. The coils 108 and 114 are typically wire antenna coils each comprised of multiple turns of electrically insulated single-strand or multi-strand platinum or gold wire. Generally, a magnet is fixed relative to each of the external coil 108 and the implantable coil 114. The magnets fixed relative to the external coil 108 and the implantable coil 114 facilitate the operational alignment of the external coil 108 with the implantable coil 114. This operational alignment of the coils enables the external component 104 to transmit data, as well as possibly power, to the implantable component 112 via a closely-coupled wireless link formed between the external coil 108 with the implantable coil 114. In certain examples, the closely-coupled wireless link is a radio frequency (RF) link. However, various other types of energy transfer, such as infrared (IR), electromagnetic, capacitive and inductive transfer, may be used to transfer the power and/or data from an external component to an implantable component and, as such, FIG. 1D illustrates only one example arrangement.

As noted above, sound processing unit 106 includes the processing module 124. The processing module 124 is configured to convert received input signals (received at one or more of the input devices 113) into output signals for use in stimulating a first ear (e.g., right ear) 141R of the recipient (i.e., the processing module 124 is configured to perform sound processing on input signals received at the sound processing unit 106). Stated differently, the one or more processors 125 are configured to execute bimodal sound processing logic 128 in memory 126 to convert the received input signals into output signals that represent electrical stimulation for delivery to the recipient. As described further below, the bimodal sound processing logic 128, when executed, operates with corresponding bimodal sound logic in the hearing aid 150 (i.e., bimodal sound processing logic 168) to map Inter-aural Level Difference (ILD) cues to inter-aural loudness difference cues for the recipient.

In the embodiment of FIG. 1D, the output signals are provided to the RF transceiver 122, which transcutaneously transfers the output signals (e.g., in an encoded manner) to the implantable component 112 via external coil 108 and implantable coil 114. That is, the output signals 145 are received at the RF interface circuitry 140 via implantable coil 114 and provided to the stimulator unit 142. The stimulator unit 142 is configured to utilize the output signals to generate electrical stimulation signals (e.g., current signals) for delivery to the recipient's cochlea via one or more stimulating contacts 144. In this way, cochlear implant 102 electrically stimulates the recipient's auditory nerve cells, bypassing absent or defective hair cells that normally transduce acoustic vibrations into neural activity, in a manner that causes the recipient to perceive one or more components of the received sound signals.

As noted above, and as shown in FIG. 1E, hearing aid 150 comprises a sound processing unit 152 and an in-the-ear (ITE) component 154. The sound processing unit 152 comprises one or more input devices 153 that are configured to receive input signals (e.g., sound or data signals). In the example of FIG. 1E, the one or more input devices 153 include one or more sound input devices 158 (e.g., microphones, audio input ports, telecoils, etc.), one or more auxiliary input devices 159 (e.g., audio ports, such as a Direct Audio Input (DAI), data ports, such as a Universal Serial Bus (USB) port, cable port, etc.), and a wireless transmitter/receiver (transceiver) 160. However, it is to be appreciated that one or more input devices 153 may include additional types of input devices and/or less input devices (e.g., the wireless transceiver 160 and/or one or more auxiliary input devices 159 could be omitted).

The sound processing unit 152 also comprises a power source 163, and a processing module 164. The processing module 164 comprises one or more processors 165 and a memory 166 that includes bimodal sound processing logic 168.

As noted, the hearing aid 150 also comprises an ITE component 154. The ITE component 154 comprises an ear mold 169 and an acoustic receiver 170 disposed in the ear mold. The ear mold 169 is configured to positioned/inserted into the ear canal of the recipient and retained therein. The acoustic receiver 170 is electrically connected to the sound processing unit 152 via a cable 171.

As noted above, sound processing unit 152 includes the processing module 164. The processing module 164 is configured to convert received input signals (received at one or more of the input devices 153) into output signals for use in stimulating the second ear (e.g., left ear) 141L of the recipient (i.e., the processing module 164 is configured to perform sound processing on input signals received at the sound processing unit 152). Stated differently, the one or more processors 165 are configured to execute bimodal sound processing logic 168 in memory 166 to convert the received input signals into processed signals that represent acoustic stimulation for delivery to the recipient.

In the embodiment of FIG. 1E, the processed signals are provided to the acoustic receiver 170 (via cable 171), which in turn acoustic stimulates the second ear 141L. That is, the processed signals, when delivered to the acoustic receiver 170, cause the acoustic receiver to deliver acoustic stimulation signals (acoustic output signals) to the ear of the recipient. The acoustic stimulation signals cause vibration of the ear drum that, in turn, induces motion of the cochlea fluid causing the recipient to perceive the input signals received at the one or more of the input devices 153. As described further below, the bimodal sound processing logic 168, when executed, operates with the corresponding bimodal sound processing logic 128 in the cochlear implant 102 to ensure that the Inter-aural Level Difference (ILD) cues are mapped reliably to inter-aural loudness difference across the two ears for the recipient.

In summary, FIGS. 1D-1E illustrate a bimodal hearing system 100 in which the first ear 141R of the recipient is electrically stimulated (e.g., electrical stimulation signals are used to evoke a hearing sensation at the first ear). However, in the bimodal hearing system 100, the second ear 141L of the recipient is acoustically stimulated (e.g., acoustic stimulation signals are used to evoke a hearing sensation at the second ear).

As noted above, in normal hearing, the main binaural cues for left/right sound localization are the Inter-aural Level Difference (ILD) and the Inter-aural Time Difference (ITD). A primary benefit of a bilateral cochlear implant system is that such systems can provide a recipient with Inter-aural Loudness differences that are consistent with the ILD cues observed. However, since the two hearing prostheses forming a bimodal system deliver different types of stimulation to the recipient, the two hearing prostheses generally use different processing strategies to generate those different types of stimulation. Due to the use of different processing strategies, the ILD measurements (measures) do not reliably map to loudness differences. That is, due to the differing processing involved at each prosthesis, existing bimodal systems do not provide recipients with correct ILD cues. For example, cochlear implants generally have a much smaller dynamic range than hearing aids and utilize different loudness growth functions. Even without any head-shadow, there are loudness mismatches across the two ears. With head-shadow, the loudness differences across the two ears becomes even more inconsistent (e.g., better in certain situations, worse in other situations, but overall inconsistent).

In a bimodal hearing system that includes a hearing aid and cochlear implant, the hearing aid and cochlear implant are typically independently "fit" (e.g., independently configured) for the recipient in order to maximize audibility. In addition, the dynamic range available for loudness perception are typically mismatched between the hearing aid and cochlear implant, the rate of growth of loudness could be different across the two ears and across different recipients, and the hearing aid and the cochlear implant process signals differently due to different design objectives. All of these mismatches make it difficult to make use of binaural cues, such as ILDs, and, accordingly, make it difficult for recipients of bimodal hearing systems to properly determine the location of the source of the sound signals. Accordingly, it would be advantageous to preserve binaural ILD cues in a bimodal hearing system, at least in certain listening environments.

As such, presented herein are techniques that enable a bimodal hearing system to provide a recipient with ILD cues, despite the different processing strategies and other mismatches between the prostheses (e.g., different dynamic ranges, different loudness growth rates, etc.). More specifically, in the example of FIGS. 1A-1E, the cochlear implant 102 and hearing aid 150 are each configured to receive sound signals and determine a corresponding loudness measures (loudness estimates) for the input signals and output signals. These estimates are, in turn, used to determine adjustments to the operation (e.g., gain settings) of one or both of the hearing aid 150 or cochlear implant 102 to ensure that the loudness differences between the sounds captured at each of the prostheses follow the ILD.

Figure 2:
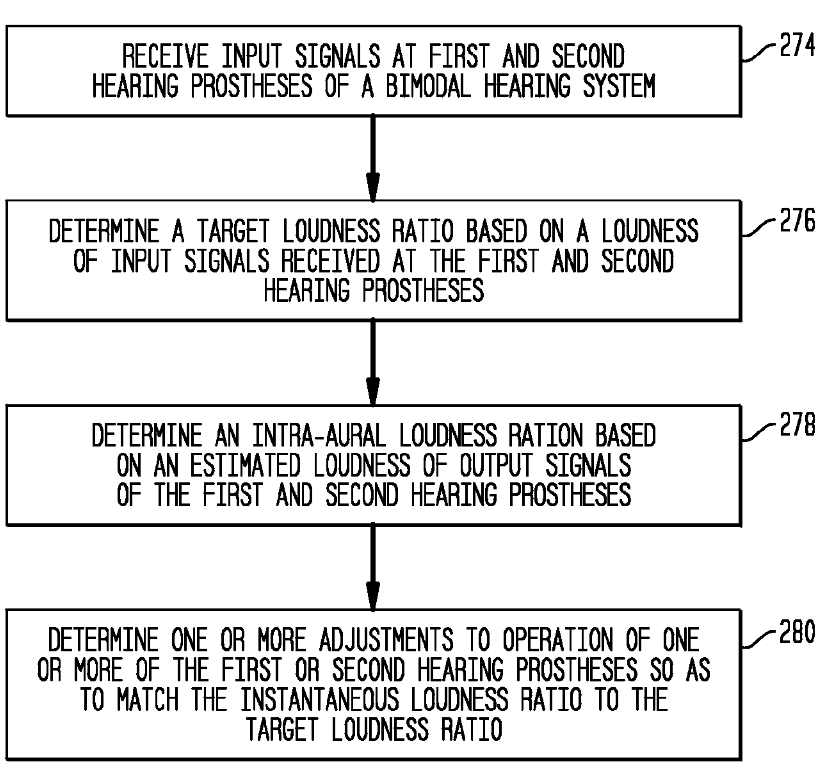
FIG. 2 is a flowchart of an example method, in accordance with certain embodiments presented herein.

FIG. 2 is flowchart of an example method 272 illustrating further details of the techniques presented herein to preserve ILD cues across both ears (both hearing prostheses) in a bimodal hearing system. For ease of description, FIG. 2 will be described with reference to bimodal hearing system 100 of FIGS. 1A-1E comprising cochlear implant 102 and hearing aid 150. However, as noted elsewhere herein, it is to be appreciated that the techniques presented herein can be implemented in other bimodal hearing systems having different prostheses, different arrangements, etc. It is also to be appreciated that specific order of steps/operations shown in FIG. 2 is illustrative and that, in certain embodiments, the steps/operations may be performed in a different order, combined, further separated, etc.

In the example of FIG. 2, method 272 begins at 274 where the hearing aid 150 and the cochlear implant 102 receive input signals (e.g., input acoustic signals). At 276, the hearing aid 150 and the cochlear implant 102 each determine a "target loudness ratio" (TLR) for the sound signals. As described further below, the target loudness ratio is determined based on the signals at the inputs of the two devices/ears and represents the loudness ratio experienced by normal hearing listeners. Stated differently, the target loudness ratio represents a ground truth measure that is relied upon to ensure the preservation of ILD cues across the two ears. The target loudness ratio is a function of the ILD measure. For binaural devices, the levels of the sound signals reaching the two ears could be different resulting in different loudness estimates at the two ears. Therefore, the target loudness ratio, which is the ratio of loudness estimates between the two ears, tracks the level differences or the ILD measure between the two ears. In other words, the ILD measures are mapped to a ratio of loudness difference and provide a ground truth for binaurally connected bimodal devices. As described earlier, hearing assisted devices have a number of limitations including limited dynamic range, different signal processing objectives, different clinical fitting to maximize audibility in each ear independently. These limitations result in the processed signals at the output of the devices have different levels/loudness compared to that observed at the input of these devices. However, measuring the ratio of loudness between the two ears enables the devices to operate within their limitations but still provide the ability adjust the levels on one or both devices such that the ratio of loudness measurements at the output of the devices matches the ratio at the input of the devices, i.e., the target loudness ratio. This enables the delivery and perception of ILD cues while still operating within the limitations of the individual devices.

In the embodiment of FIG. 2, the target loudness ratio is determined at each of the hearing aid 150 and the cochlear implant 102. The target loudness ratio determined at the cochlear implant 102 is referred to as the cochlear implant target loudness ratio ($TLR_{CI}$) and the target loudness ratio determined at the hearing aid 150 is referred to as the hearing aid target loudness ratio ($TL_{RXA}$). It is to be appreciated that, in certain embodiments, the target loudness ratio may be determined at only the hearing aid 150 or only the cochlear implant 102.

At 278, the hearing aid 150 and the cochlear implant 102 determine an estimated "instantaneous loudness ratio" or "inter-aural loudness ratio" of the loudness of the acoustic and electrical output signals generated from the sound signals at the hearing aid 150 and the cochlear implant 102, respectively. That is, as described further below, the inter-aural loudness ratio is an estimated loudness ratio for the acoustic output signals and electrical output signals generated from the input at the hearing aid 150 and the cochlear implant 102, respectively The inter-aural loudness ratio can be determined at each of the hearing aid 150 and the cochlear implant 102 and inter-aural loudness ratio determined at the cochlear implant 102 is referred to as the cochlear implant inter-aural loudness ratio ($ILoR_{CI}$) and the inter-aural loudness ratio determined at the hearing aid 150 is referred to as the hearing aid inter-aural loudness ratio ($ILoR_{HA}$). It is to be appreciated that, in certain embodiments, the inter-aural loudness ratio may be determined at only the hearing aid 150 or only the cochlear implant 102.

At 280, the hearing aid 150 and/or the cochlear implant 102 determines one or more adjustments to the sound processing settings in order to match the inter-aural loudness ratio to the target loudness ratio (e.g., determine one or more adjustments to the device operations so that the inter-aural loudness ratio and the target loudness ratio are substantially the same). In certain embodiments, the hearing aid 150 and/or the cochlear implant 102 can adjust the gain settings used to generate output signals (the acoustic or electrical stimulation signals) in order to match the instantaneous loudness ratio to the target loudness ratio.

It is to be appreciated that the operations performed at each of 276, 278, and 280 may include or use information from one or both of the hearing aid 150 and/or the cochlear implant 102. As noted above, the bimodal hearing system 100 includes a bidirectional communication channel 148 that can be used to exchange any information/data, as needed, between the hearing aid 150 and the cochlear implant 102 for use in these and other operations. For ease of description, the steps for exchanging data between the hearing aid 150 and the cochlear implant 102 have generally been omitted herein.

Figure 3:
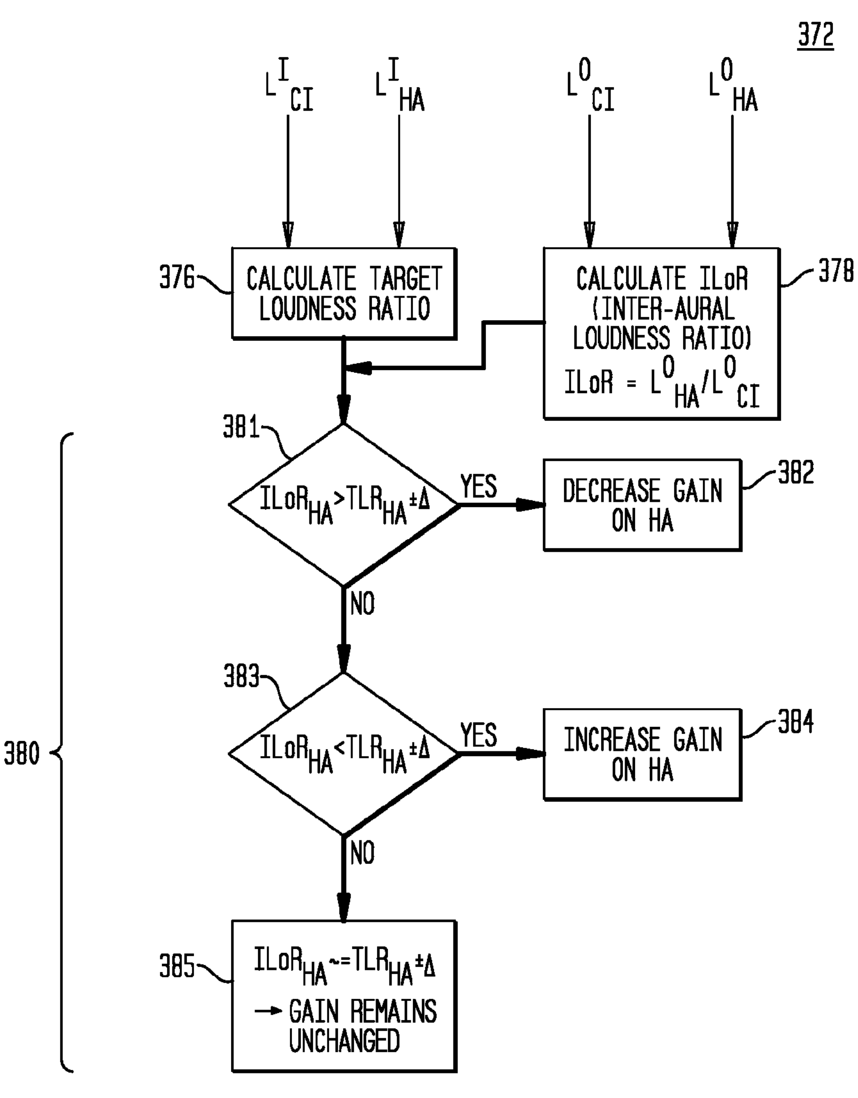
FIG. 3 is flowchart illustrating another example method, in accordance with certain embodiments presented herein.
Figure 4:
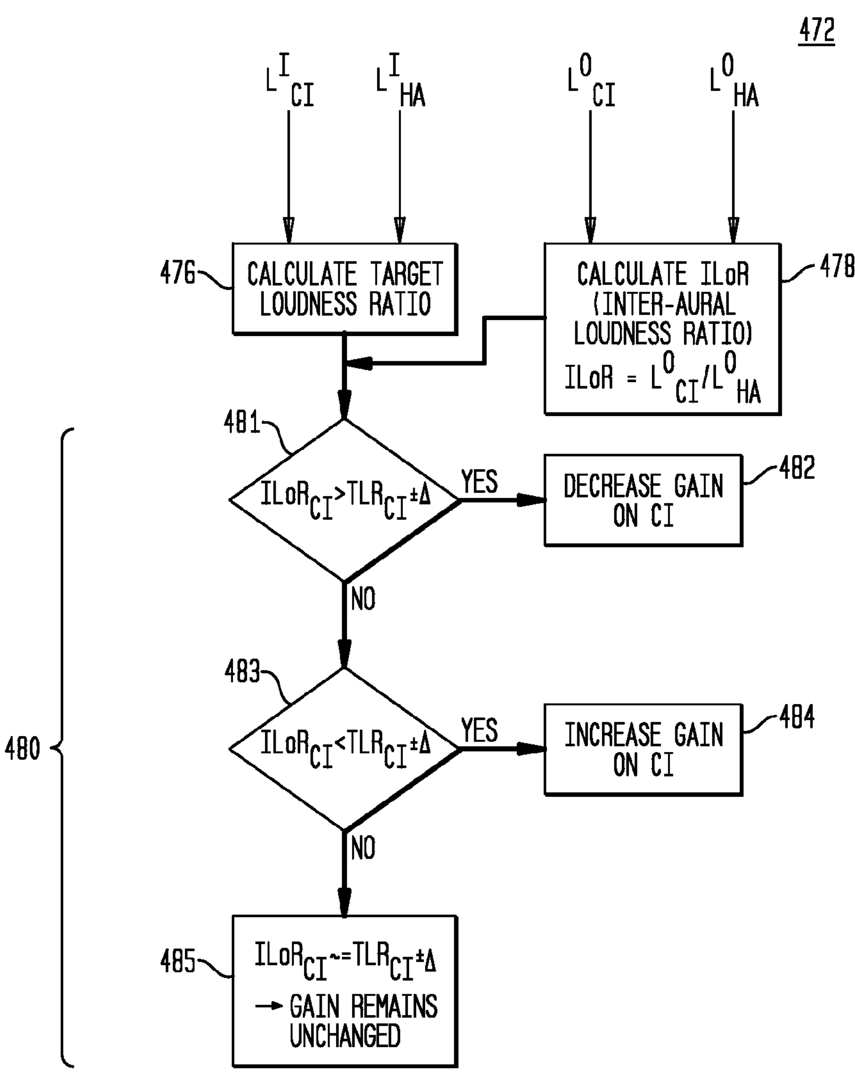
FIG. 4 is flowchart illustrating another example method, in accordance with certain embodiments presented herein.

Further details of the operations performed at each of 276, 278, and 280 are provided below. More specifically, FIG. 3 is a flowchart illustrating further details of aspects of the method 272 performed at hearing aid 150, while FIG. 4 is a flowchart further details of aspects of the method 272 performed at cochlear implant 102. For ease of description, the method shown in FIG. 3 will be referred to as method 372, while the method shown in FIG. 4 will be referred to as method 472. In these examples, methods 372 and 472 are performed in parallel (e.g., in real-time) at the hearing aid 150 and the cochlear implant 102, respectively. It is to be appreciated that, in alternative embodiments, only the method 372 or only the method 472 could be performed to preserve the ILD cues.

Referring first to FIG. 3, method 372 begins at 376 where the hearing aid 150 (e.g., one or more processors 165 executing bimodal sound processing logic 168) calculates/determines a hearing aid target loudness ratio ($TLR_{HA}$). As shown, the hearing aid 150 calculates the hearing aid target loudness ratio from the loudness at the input of the hearing aid ($L^I_{HA}$) and the loudness at the input of the cochlear implant ($L^I_{CI}$) (e.g., from the loudness of the input signals received at each of the hearing aid 150 and the cochlear implant 102). The loudness of the input signals received at the hearing aid ($L^I_{HA}$) and the loudness of the input signals received at the cochlear implant ($L^I_{CI}$) are determined at the hearing aid 150 and cochlear implant 102, respectively, and exchanged via the bilateral communication channel 148.

At 378, the hearing aid 150 calculates/determines a hearing aid inter-aural loudness ratio ($ILoR_{HA}$). As shown, the hearing aid 150 calculates the hearing aid inter-aural loudness ratio from the estimated acoustic output loudness of the hearing aid ($L^O_{HA}$) and the estimated output loudness of the cochlear implant ($L^O_{CI}$). The estimated acoustic output loudness of the hearing aid ($L^O_{HA}$), which is sometimes referred to herein as the acoustic output loudness, is the estimated loudness of the acoustic output signals generated at the hearing aid 150 from the input signals (i.e., the output loudness after hearing aid processing). The estimated output loudness of the cochlear implant ($L^O_{CI}$), which is sometimes referred to herein as the electric output loudness, is the estimated loudness of the electrical output signals generated at the cochlear implant 102 from the input signals (i.e., the output loudness after cochlear implant processing). The estimated output loudness of the hearing aid ($L^O_{HA}$) and the estimated output loudness at of the cochlear implant ($L^O_{CI}$) are determined at the hearing aid 150 and cochlear implant 102, respectively, and exchanged via the bilateral communication channel 148.

At 380, the hearing aid target loudness ratio ($TLR_{HA}$) and the inter-aural loudness ratio ($ILoR_{HA}$) are used to determine whether operations/settings of the hearing aid 150 should be adjusted to make the inter-aural loudness ratio ($ILoR_{HA}$) match the hearing aid target loudness ratio ($TLR_{HA}$). That is, as noted above, the hearing aid target loudness ratio ($TLR_{HA}$) represents a loudness ratio that, if present between the acoustic stimulation signals and electrical stimulation signals delivered to the recipient at the hearing aid 150 and cochlear implant 102, respectively, will provide the recipient with ILD cues enabling the recipient to locate (e.g., determine a source direction for) the input signals. In contrast, the inter-aural loudness ratio ($ILoR_{HA}$) represents a loudness ratio that is estimated to be present at the output of the hearing aid 150. Accordingly, the techniques presented herein operate to adjust operation of the hearing aid 150 (or the cochlear implant 102), as needed, to make the inter-aural loudness ratio ($ILoR_{HA}$) substantially match the hearing aid target loudness ratio ($TLR_{HA}$). As used herein, "substantially matching" the inter-aural loudness ratio ($ILoR_{HA}$) to the hearing aid target loudness ratio ($TLR_{HA}$) refers to adjusting operation of the hearing aid 150 and/or the cochlear implant 102 such that the inter-aural loudness ratio ($ILoR_{HA}$) is within a selected (e.g., predetermined) numerical range of the hearing aid target loudness ratio ($TLR_{HA}$).

Returning to the specific example of FIG. 3, the operations of 380 first include operations at 381 where the hearing aid 150 determines whether the inter-aural loudness ratio ($ILoR_{HA}$) is greater than the hearing aid target loudness ratio ($TLR_{HA}$) by a selected amount (A). If the inter-aural loudness ratio ($ILoR_{HA}$) is greater than the hearing aid target loudness ratio ($TLR_{HA}$) by more than the selected amount, then method 372 proceeds to 382 where the gain used by the hearing aid 150 to generate acoustic stimulation signals from the input signals is decreased/reduced.

If it is determined at 381 that the inter-aural loudness ratio ($ILoR_{HA}$) is not greater than the hearing aid target loudness ratio ($TLR_{HA}$) by more than the selected amount, then method 372 proceeds to 383 where the hearing aid 150 determines whether the inter-aural loudness ratio ($ILoR_{HA}$) is less than the hearing aid target loudness ratio ($TLR_{HA}$) by the same or different selected amount (A). If the inter-aural loudness ratio ($ILoR_{HA}$) is less than the hearing aid target loudness ratio ($TLR_{HA}$) by more than the selected amount, then method 372 proceeds to 384 where the gain used by the hearing aid 150 to generate acoustic stimulation signals from the input signals is increased.

If it is determined at 383 that the inter-aural loudness ratio ($ILoR_{HA}$) is not less than the hearing aid target loudness ratio ($TLR_{HA}$) by more than the selected amount, then method 372 proceeds to 385 where the gain used by the hearing aid 150 to generate acoustic stimulation signals from the input signals remains unchanged.

As noted, in the specific example of FIG. 3, the operations of 380 are shown as comprising operations 381, 382, 383, 384, and 385. It is to be appreciated that this specific separation and order of operations is merely illustrative and that the operations at 380 can be performed in a different order, combined, further separated, include additional operations, etc. For example, the determinations at 381 and 383 could be combined into a single determination with a resulting action corresponding to either 382 or 384.

Referring next to FIG. 4, method 472 begins at 476 where the cochlear implant 102 (e.g., one or more processors 125 executing bimodal sound processing logic 128) calculates/determines a cochlear implant target loudness ratio ($TLR_{CI}$). As shown, the cochlear implant 102 calculates the cochlear implant target loudness ratio from the loudness at the input of the hearing aid ($L^I_{HA}$) and the loudness at the input of the cochlear implant ($L^I_{CI}$) (e.g., from the loudness of the input signals received at each of the hearing aid 150 and the cochlear implant 102). As noted above, the loudness of the input signals received at the hearing aid ($L^I_{HA}$) and the loudness of the input signals received at the cochlear implant ($L^I_{CI}$) are determined at the hearing aid 150 and cochlear implant 102, respectively, and exchanged via the bilateral communication channel 148.

At 478, the cochlear implant 102 calculates/determines a cochlear implant inter-aural loudness ratio ($ILoR_{CI}$). As shown, the cochlear implant 102 calculates the cochlear implant inter-aural loudness ratio from the estimated output loudness of the hearing aid ($L^O_{HA}$) and the estimated output loudness of the cochlear implant ($L^O_{CI}$). As noted above, the estimated output loudness of the hearing aid ($L^O_{HA}$) and the estimated output loudness at of the cochlear implant ($L^O_{CI}$) are determined at the hearing aid 150 and cochlear implant 102, respectively, and exchanged via the bilateral communication channel 148.

At 480, the cochlear implant target loudness ratio ($TLR_{CI}$) and the inter-aural loudness ratio ($ILoR_{CI}$) are used to determine whether settings/operations of the cochlear implant 102 (or hearing aid 150) should be adjusted to make the inter-aural loudness ratio ($ILoR_{CI}$) match the cochlear implant target loudness ratio ($TLR_{CI}$). That is, as noted above, the cochlear implant target loudness ratio ($TLR_{CI}$) represents a loudness ratio that, if present between the acoustic stimulation signals and electrical stimulation signals delivered to the recipient at the hearing aid 150 and cochlear implant 102, respectively, will provide the recipient with ILD cues enabling the recipient to locate (e.g., determine a source direction for) the input signals. In contrast, the inter-aural loudness ratio ($ILoR_{CI}$) represents a loudness ratio that is estimated to be present at the output of the cochlear implant 102. Accordingly, the techniques presented herein operate to adjust operation of the cochlear implant 102 (or the hearing aid 150), as needed, to make the inter-aural loudness ratio ($ILoR_{CI}$) substantially match the hearing aid target loudness ratio ($TLR_{CI}$).

In the specific example of FIG. 4, the operations of 480 first include operations at 481 where the cochlear implant 102 determines whether the inter-aural loudness ratio ($ILoR_{CI}$) is greater than the cochlear implant target loudness ratio ($TLR_{CI}$) by a selected amount (A). If the inter-aural loudness ratio ($ILoR_{CI}$) is greater than the hearing aid target loudness ratio ($TLR_{CI}$) by more than the selected amount, then method 472 proceeds to 482 where the gain used by the cochlear implant 102 to generate electrical stimulation signals from the input signals is decreased/reduced.

If it is determined at 481 that the inter-aural loudness ratio ($ILoR_{CI}$) is not greater than the hearing aid target loudness ratio ($TLR_{CI}$) by more than the selected amount, then method 472 proceeds to 483 where the cochlear implant 102 determines whether the inter-aural loudness ratio ($ILoR_{CI}$) is less than the cochlear implant target loudness ratio ($TLR_{CI}$) by the same or different selected amount (A). If the inter-aural loudness ratio ($ILoR_{CI}$) is less than the cochlear implant target loudness ratio ($TLR_{CI}$) by more than the selected amount, then method 472 proceeds to 484 where the gain used by the cochlear implant 102 to generate electrical stimulation signals from the input signals is increased.

If it is determined at 483 that the inter-aural loudness ratio ($ILoR_{CI}$) is not less than the hearing aid target loudness ratio ($TLR_{CI}$) by more than the selected amount, then method 472 proceeds to 485 where the gain used by the cochlear implant 102 to generate electrical stimulation signals from the input signals remains unchanged.

As noted, in the specific example of FIG. 4, the operations of 480 are shown as comprising operations 481, 482, 483, 484, and 485. It is to be appreciated that this specific separation and order of operations is merely illustrative and that the operations at 480 can be performed in a different order, combined, further separated, include additional operations, etc. For example, the determinations at 481 and 483 could be combined into a single determination with a resulting action corresponding to either 482 or 484.

Merely for ease of description, methods 372 and 472 have been described substantially independently. However, it is to be appreciated that, in certain embodiments, the methods 372 and 472 can be performed substantially in parallel and/or cooperatively. For example, the hearing aid 150 and cochlear implant 102 could exchange data indicating the adjustments made to the processing settings (e.g., gain), or data indicating potential or proposed adjustments to the processing settings. This information could be used by the hearing aid 150 and/or cochlear implant 102 to determine whether adjustments to the processing settings should be made and/or how to determine the amount of adjustments to be made.

For example, cochlear implant 102 could determine, at 481, that the inter-aural loudness ratio ($ILoR_{CI}$) is greater than the cochlear implant target loudness ratio ($TLR_{CI}$) by a selected amount (A) and that a decrease in gain should be implemented at 482. However, before decreasing the gain, the cochlear implant 102 could receive data indicating that the hearing aid 150 has increased, or intends to, increase the gain used at the hearing aid 150. As such, the cochlear implant 102 could determine that no gain decrease at the cochlear implant 102 is necessary and/or determine that a smaller gain decrease should be implemented. In such embodiments, the hearing aid 150 and the cochlear implant 102 could operate in a master-slave type of arrangement where one of the devices (e.g., the cochlear implant) reacts to the adjustments made at the other device.

As noted, FIGS. 3 and 4 have generally been described as performing the techniques presented herein at each prosthesis in the bimodal hearing system 100. However, it is to be appreciated that, in certain embodiments, the techniques presented herein could be performed at only one of the prostheses. For example, the cochlear implant 102 could be configured to operate without performing the techniques presented herein, while method 372 is implemented at the hearing aid 150. In such an example, only the hearing aid 150 would adjust settings/operations in order to match the inter-aural loudness ratio ($ILoR_{HA}$) to the loudness ratio ($TLR_{HA}$). The cochlear implant 102 would still provide data to the hearing aid 150 for use in determining the inter-aural loudness ratio ($ILoR_{HA}$) and/or the target loudness ratio ($TLR_{HA}$).

In general, the ILDs and/or loudness measures can be exchanged across the two ears, as needed, to have ground truth information and to make the necessary modifications in the respective ears. However, it is to be appreciated that the loudness calculations need not happen continuously and, instead, can be determined periodically, and/or when there is a change in the acoustic environment detected by the cochlear implant 102 and/or the hearing aid 150. Changes in the acoustic environment can include, for example, a change in speaker, a change in speaker location, detection of additional speakers, detection of background noise, detection of a change in background noise, a change of the sound classification, etc.

As noted above, one or more settings/operations of the cochlear implant 102 and/or the hearing aid 150 can be adjusted to order to match the inter-aural loudness ratio (ILoR) to the target loudness ratio (TLR). In certain embodiments, the gain settings of the cochlear implant 102 and/or the hearing aid 150 are adjusted in order to match the inter-aural loudness ratio (ILoR) to the loudness ratio (TLR). The gain setting adjustments can be broadband gain adjustments (e.g., adjust gain settings across the frequency spectrum) or narrowband gain adjustments (e.g., adjust gain only in one or more select frequency bands). The narrowband gain adjustments could be made, for example, only in frequency bands that that have larger dynamic ranges at each of the prostheses.

Although the gain adjustments are generally made in order to match the inter-aural loudness ratio (ILoR) to the loudness ratio (TLR), the gain adjustments could also be influenced/controlled by other factors. For example, the gain adjustments can be further based: on the dynamic range at either the cochlear implant 102/or the hearing aid 150; recipient preferences (e.g., could be the ear with limited dynamic range); signal-to-noise ratio (SNR) measurements, location of background noises, location of sound sources, etc.

It is to be appreciated that saturation occurs when the gains cannot be adjusted further since the loudness measures are reaching the saturation limits possible with that device. In certain embodiments, the cochlear implant 102 and hearing aid 150 can be configured to detect when saturation occurs and transmit a saturation notification to the contralateral prostheses. The saturation notification indicates that the gains cannot be adjusted anymore on the device and requests the opposite device to one of the devices. In certain embodiments, the signals could also be scaled by the same factor on both sides to obtain additional headroom to attain a target loudness ratio.

In certain embodiments, look-up tables may be stored on the hearing aid 150 and/or the cochlear implant 102 map dBSPL levels in narrowband channels to loudness. These values could be measured for each recipient and stored in memory and used to perform one or more operations of FIG. 2, 3, or 4 in (e.g., accomplish some of the steps described above faster and/or with less processing).

In general, the techniques presented herein operate on the premise that the normal hearing loudness target may not be achievable for all recipients and across both ears in a bimodal hearing system. As such, instead of preserving the actual loudness, the loudness ratio between the ears is preserved. Therefore, the gains (or other settings) are adjusted on both sides such that the resulting loudness falls within the dynamic range of each ear and result in the same loudness ratio as obtained with the original loudness measure across both ears. The result is the ability to provide binaural ILD cues, albeit possibly at the expense of reduced audibility in one or both ears.

For example, "sone" is a unit of loudness that measures the perceived loudness of the sound, i.e., it measures a subjective characteristic of sound as opposed to objective scales of measurement such as dB SPL (Sound Pressure Level). One sone is defined as the loudness of a 1 kHz tone at 40 dB SPL. On the sone scale, a tone judged by the listener to be twice as loud would have a loudness of 2 sones, three times as loud would be 3 sones and so forth. For example, a 1 kHz tone that is 2 sones is twice as loud as a 1 kHz tone that is 1 sone loud. Similarly, a 1 kHz tone that is 4 sones is twice as loud as the 2 sones tone or four times as loud as the 1 sone tone.

In one example of the techniques presented herein, the true loudness of the stimulus on the left and right ears are each eight (8) sones and four (4) sones respectively (i.e., a target loudness ratio of 2 on the left ear). If the dynamic range of the left ear can only reach 6 sones for that particular stimuli, the gains will be adjusted such that the loudness on the right ear is 3 sones so that the same ratio of loudness is maintained across the ears.

Figure 5:
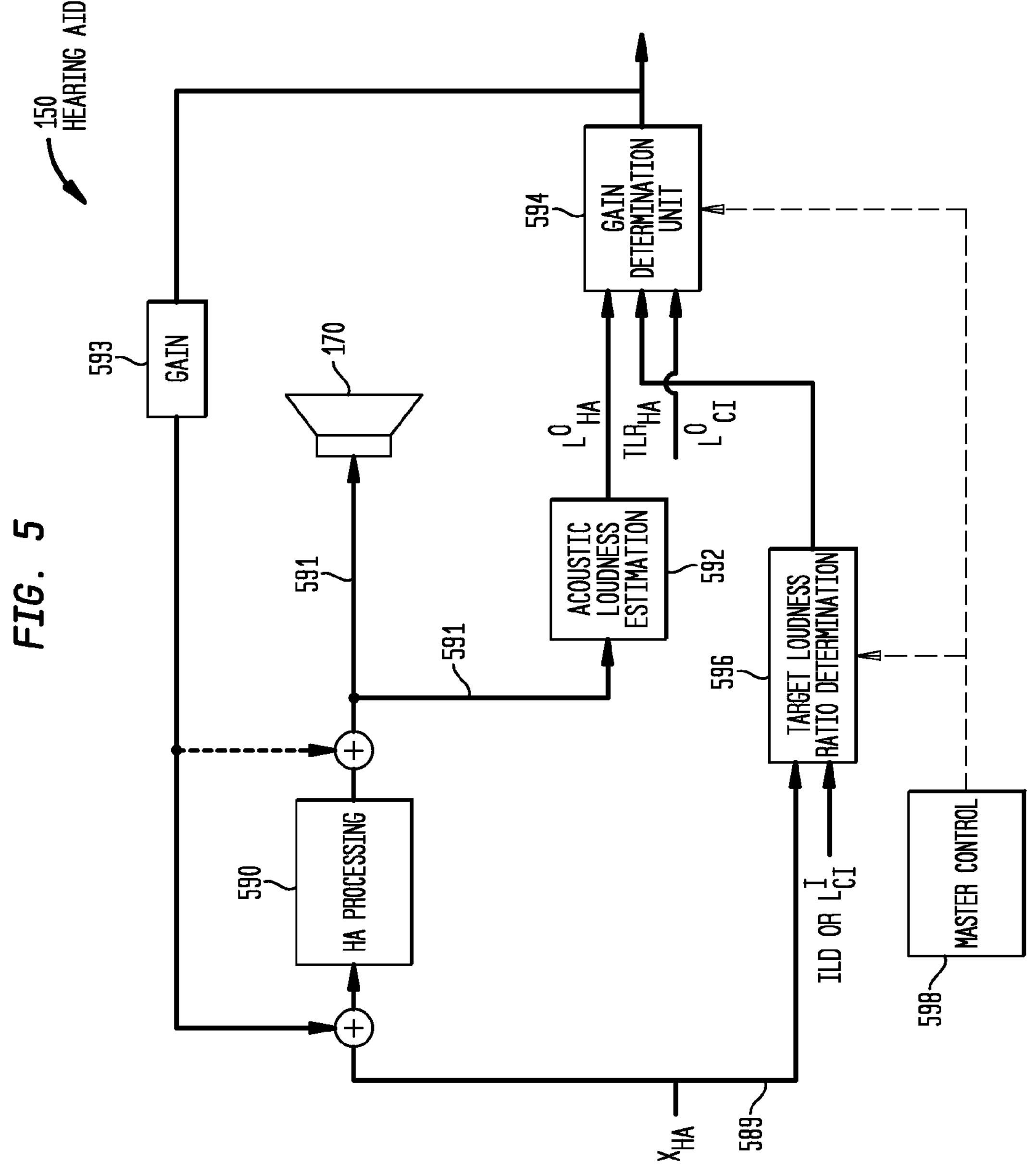
FIG. 5 is a functional block diagram of an example hearing prosthesis forming part of a bimodal hearing system, in accordance with certain embodiments presented herein.

FIG. 5 is a functional block diagram illustrating the functional blocks of hearing aid 150 configured to implement the techniques presented herein (e.g., a functional arrangement for processing module 164 and the execution of bimodal sound processing logic 168). In particular, FIG. 5 illustrates the functional blocks of hearing aid 150 that are configured to perform the operations of method 372 described above with reference to FIG. 3.

As shown, in this example, the hearing aid 150 functionally comprises a hearing aid (HA) processing block/module 590, an acoustic loudness estimation block 592, a gain determination unit 594, a target loudness ratio determination block 596, and a master control block 598. Also shown in FIG. 5 is the acoustic receiver 170.

In the embodiment of FIG. 5, input signals ($X_{HA}$) 589 are received at one or more sound input devices of the hearing aid 150 and provided to the hearing aid processing block 590. The input signals 589 are also provided to the target loudness ratio determination block 596.

The hearing aid processing block 590 processes the input signals (e.g., in accordance predetermined sound processing settings) and generates processed signals 591. The processed signals 591 are provided to the acoustic receiver 170 for delivery to the recipient, as well as to the acoustic loudness estimation block 592. The acoustic loudness estimation block 592 is configured to determine/calculate the acoustic output loudness of the hearing aid ($L^{O}_{HA}$) using an acoustic loudness model.

As noted, the input signals 589 are provided to the target loudness ratio determination block 596. The target loudness ratio determination block 596 is configured to determine the hearing aid target loudness ratio ($TLR_{HA}$) based, in part, on the input signals 589. As described further below, in certain embodiments, the target loudness ratio determination block 596 may be configured to determine the hearing aid target loudness ratio based on the input signals 589 and a determined ILD. Alternatively, also as described further below, the target loudness ratio determination block 596 may be configured to determine the hearing aid target loudness ratio based on the input signals 589, the loudness of the input signals received at the hearing aid ($L^{I}_{HA}$), and the loudness of the input signals received at the cochlear implant ($L^{I}_{CI}$). The determination of the hearing aid target loudness ratio at the target loudness ratio determination block 596 can also be controlled by, or based on, signals/data from the master control block 598.

The determined hearing aid target loudness ratio is provided to the gain determination unit 594, along with the acoustic output loudness ($L^{O}_{HA}$) and the electric output loudness ($L^{O}_{CI}$). As noted above, the acoustic output loudness and electric output loudness are used to generate the inter-aural loudness ratio ($ILoR_{HA}$), which is used along with the hearing aid target loudness ratio ($TLR_{HA}$) to determine whether adjustments to operation of the hearing aid are needed in order to preserve the ILD cues associated with the input signals 589. The determination at block 594 can also be controlled by, or based on, signals/data from the master control block 598.

In the example of FIG. 5, the inter-aural loudness ratio ($ILoR_{HA}$) and the hearing aid target loudness ratio ($TLR_{HA}$) are used to determine a gain 593 for use in generating the processed signals 591. As described above, the gain 593 generated by the gain determination unit 594 may be an adjusted gain (e.g., increased gain or a decreased gain) that is used to match the inter-aural loudness ratio ($ILoR_{HA}$) to the hearing aid target loudness ratio ($TLR_{HA}$). As shown in FIG. 5, the gain 593 could be applied either before or after the hearing aid processing block 590. The advantages of applying the gain 593 before the hearing aid processing is that the gain 593 is applied before the input signals 589 go through the predetermined hearing aid gain prescriptions for the modified level of the signal. This ensures that the gain 593 is processed in accordance with the individual hearing characteristics of the recipient and that that the gain 593 does not result in a uniform increase in the level of the signal across all frequency regions. In addition, hearing aid processing generally include algorithms to ensure that the output signals are below the maximum possible output (MPO).

Figure 6:
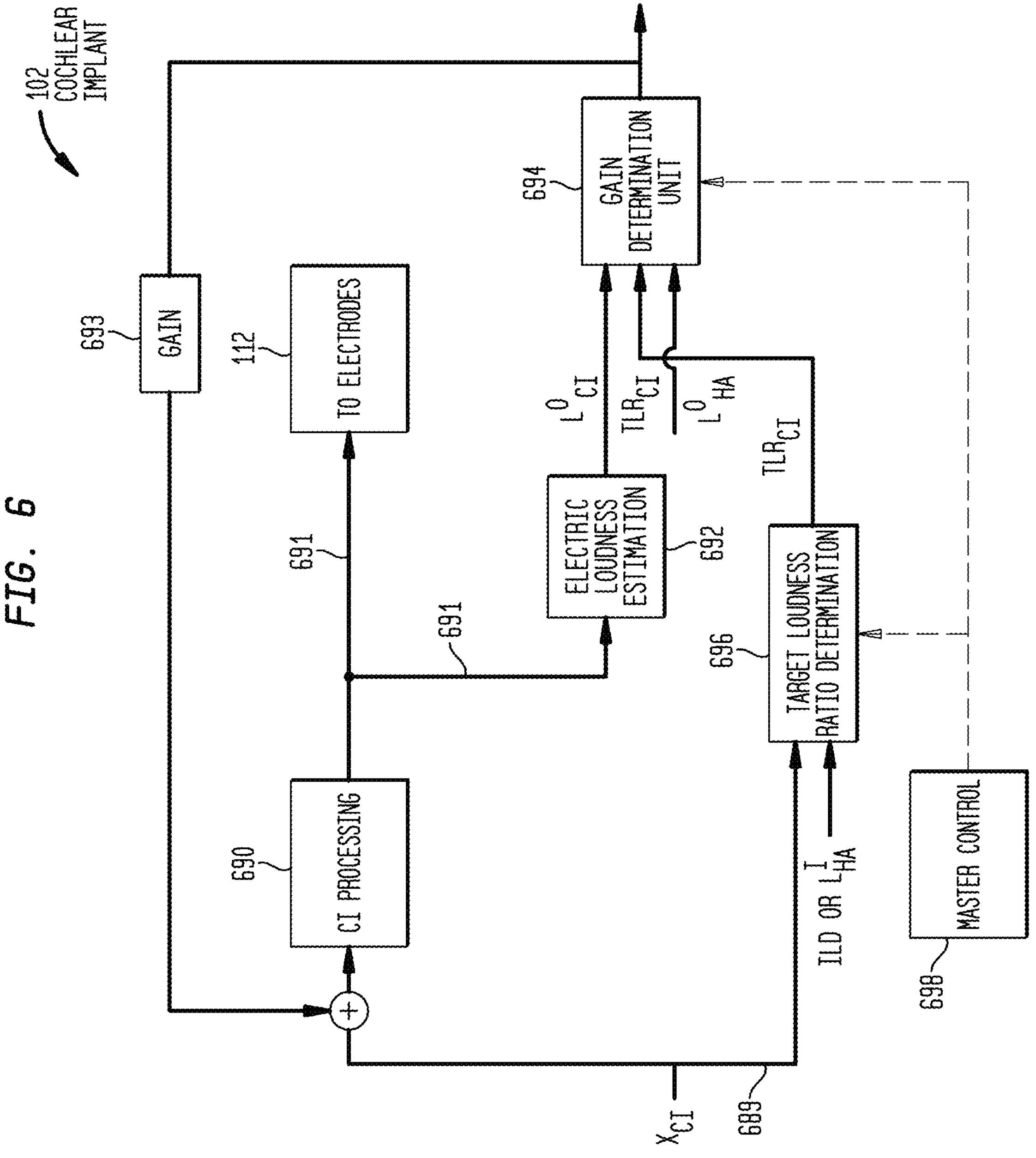
FIG. 6 is a functional block diagram of an example hearing prosthesis forming part of a bimodal hearing system, in accordance with certain embodiments presented herein.

FIG. 6 is a functional block diagram illustrating the functional blocks of cochlear implant 102 configured to implement the techniques presented herein (e.g., a functional arrangement for processing module 124 and the execution of bimodal sound processing logic 128). In particular, FIG. 6 illustrates the functional blocks of cochlear implant 102 that are configured to perform the operations of method 472 described above with reference to FIG. 4.

As shown, in this example, the cochlear implant 102 functionally comprises a cochlear implant (CI) processing block/module 690, an electric loudness estimation block 692, a gain determination unit 694, a target loudness ratio determination block 696, and a master control block 698. Also shown in FIG. 6 is a block representing the implantable component 112 of the cochlear implant 102.

As shown in FIG. 6, input signals ($X_{CI}$) 689 are received at one or more sound input devices of the cochlear implant 102 and provided to the cochlear implant processing block 690. The input signals 689 are also provided to the target loudness ratio determination block 696.

The cochlear implant processing block 690 processes the input signals (e.g., in accordance predetermined sound processing settings) and generates processed signals 691. The processed signals 691 are provided to the implantable component 112 for use in generating electrical stimulation signals for delivery to the recipient, as well as to the electric loudness estimation block 692. The electric loudness estimation block 692 is configured to determine/calculate the electric output loudness of the cochlear implant ($L^{O}_{CI}$) using an electric loudness model.

As noted, the input signals 689 are provided to the target loudness ratio determination block 696. The target loudness ratio determination block 696 is configured to determine the cochlear implant target loudness ratio ($TLR_{CI}$) based, in part, on the input signals 689. As described further below, in certain embodiments, the target loudness ratio determination block 696 may be configured to determine the cochlear implant target loudness ratio based on the input signals 689 and a determined ILD. Alternatively, also as described further below, the target loudness ratio determination block 696 may be configured to determine the cochlear implant target loudness ratio based on the input signals 689, the loudness of the input signals received at the cochlear implant ($L^{I}_{HA}$), and the loudness of the input signals received at the cochlear implant ($L^{I}_{CI}$). The determination of the cochlear implant target loudness ratio at the target loudness ratio determination block 696 can also be controlled by, or based on, signals/data from the master control block 698.

The determined cochlear implant target loudness ratio is provided to the gain determination unit 694, along with the acoustic output loudness ($L^{O}_{HA}$) and the electric output loudness ($L^{O}_{CI}$). As noted above, the acoustic output loudness and electric output loudness are used to generate the inter-aural loudness ratio ($ILoR_{CI}$), which is used along with the cochlear implant target loudness ratio ($TLR_{CI}$) to determine whether adjustments to operation of the cochlear implant are needed in order to preserve the ILD cues associated with the input signals 689. The determination at block 694 can also be controlled by, or based on, signals/data from the master control block 698.

In the example of FIG. 6, the inter-aural loudness ratio ($ILoR_{CI}$) and the cochlear implant target loudness ratio ($TLR_{CI}$) are used to determine a gain 693 for use in generating the processed signals 691. As described above, the gain 693 generated by the gain determination unit 694 may be an adjusted gain (e.g., increased gain or a decreased gain) that is used to match the cochlear implant inter-aural loudness ratio ($ILoR_{CI}$) to the cochlear implant target loudness ratio ($TLR_{HA}$). As shown in FIG. 6, the gain 693 is applied before the cochlear implant processing block 690. This is because it could be a safety hazard to increase the current levels at the output of the cochlear implant 102.

Figure 7:
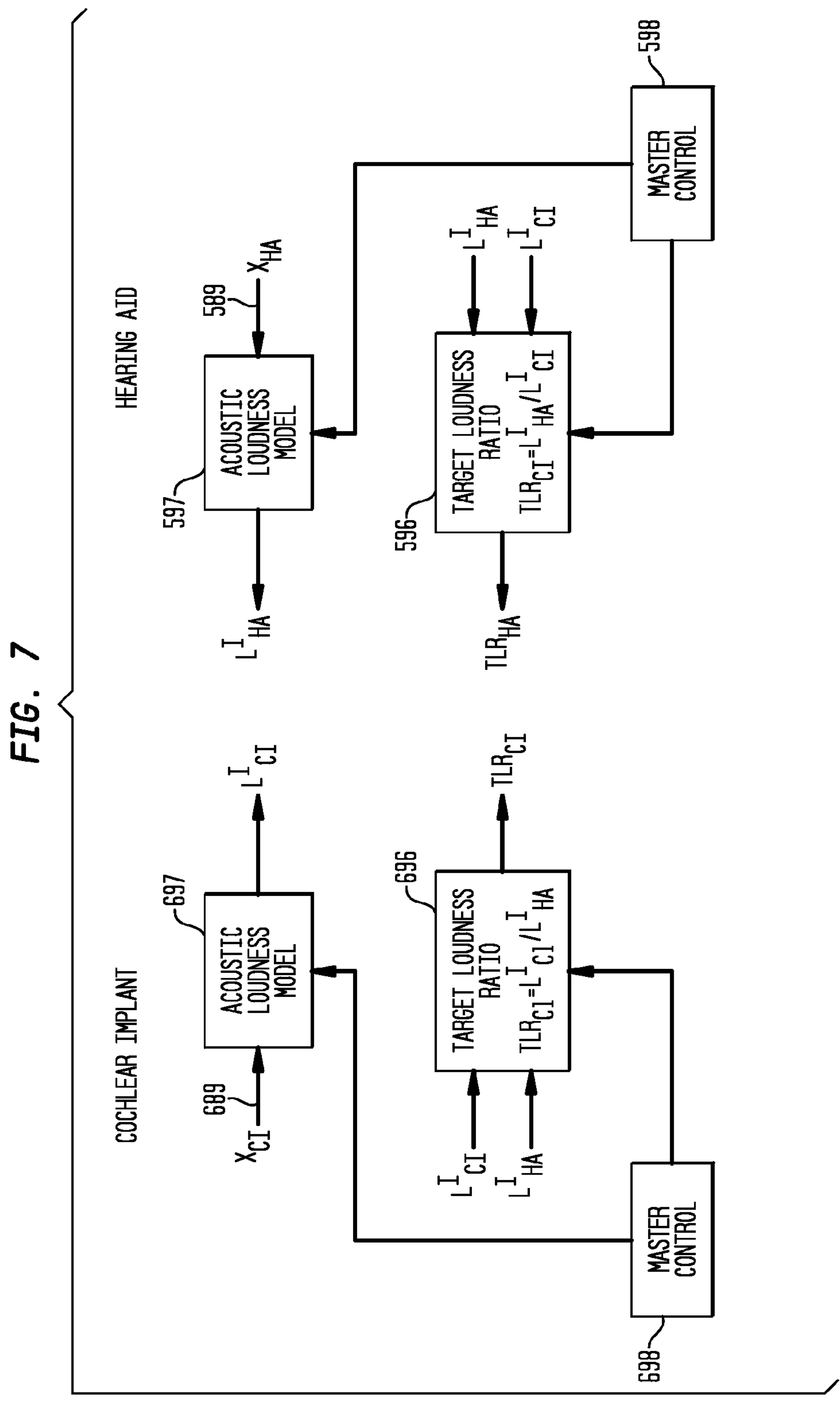
FIG. 7 is functional block diagram illustrating techniques for determination of target loudness ratios for a hearing aid and a cochlear implant in a bimodal hearing system, in accordance with certain embodiments presented herein.

As noted above in FIGS. 5 and 6, the target loudness ratios ($TLR_{HA}$ and $TLR_{CI}$) can be determined in a number of different manners. FIG. 7 is functional block diagram illustrating determination/calculation of the target loudness ratios ($TLR_{HA}$ and $TLR_{CI}$) independently at the hearing aid 150 and cochlear implant 102. In this example, the input signals 589 and 689 are received at the hearing aid 150 and cochlear implant 102, respectively. The hearing aid 150 determines the acoustic loudness ($L^I_{HA}$) of the input signals 589 received at the hearing aid, while the cochlear implant 102 determines the acoustic loudness ($L^I_{CI}$) of the input signals 689 received at the cochlear implant. These determinations are each made using acoustic loudness models 597 and 697, respectively.

The loudness of the input signals received at the hearing aid ($L^I_{HA}$) and the loudness of the input signals received at the cochlear implant ($L^I_{CI}$) are determined at the hearing aid 150 and cochlear implant 102, respectively, are exchanged by the two prostheses via the bilateral communication channel 148. After this data exchange, the hearing aid 150 and cochlear implant 102 each determine their respective target loudness ratio directly from the acoustic loudness ($L^I_{HA}$) of the input signals 589 and the acoustic loudness ($L^I_{CI}$) of the input signals 689. For example, as shown in FIG. 7, the cochlear implant target loudness ratio ($TLR_{CI}$) is determined by dividing the acoustic loudness ($L^I_{CI}$) of the input signals 689 by the acoustic loudness ($L^I_{HA}$) of the input signals 589. The hearing aid target loudness ratio ($TLR_{HA}$) is determined by dividing the acoustic loudness ($L^I_{HA}$) of the input signals 589 by the acoustic loudness ($L^I_{CI}$) of the input signals 689.

As noted above, these loudness calculations need not happen continuously and, instead, can be determined periodically, and/or when there is a change in the acoustic environment detected by the cochlear implant 102 and/or the hearing aid 150. Changes in the acoustic environment can include, for example, a change in speaker, a change in speaker location, detection of additional speakers, detection of background noise, detection of a change in background noise, a change of the sound classification, etc.

Figure 8:
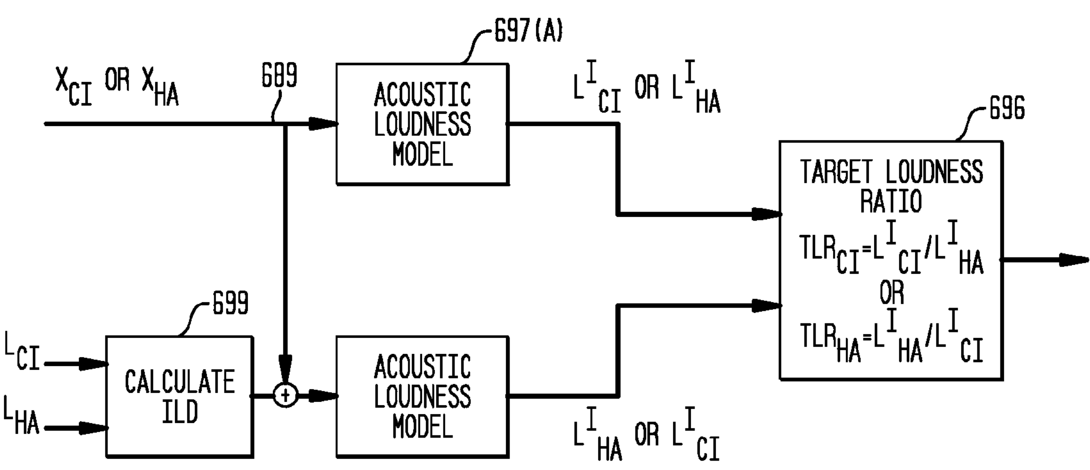
FIG. 8 is functional block diagram illustrating alternative techniques for determination of target loudness ratios for a hearing aid and a cochlear implant in a bimodal hearing system, in accordance with certain embodiments presented herein.

FIG. 8 is functional block diagram illustrating another technique for determination/calculation of the target loudness ratios ($TLR_{HA}$ and $TLR_{CI}$) based on the ILD of the input signals 589 and 689. In particular, FIG. 8 illustrates the operations that can performed at either or both of the hearing aid 150 and/or the cochlear implant 102. Merely for ease of illustration, FIG. 8 will be described with reference to cochlear implant 102 (e.g., elements of FIG. 6).

In the example of FIG. 8, an acoustic loudness model 697(A) is configured to determine the acoustic loudness ($L^I_{CI}$) of the input signals 689 received at the cochlear implant 102. The acoustic loudness ($L^I_{CI}$) is provided to the target loudness ratio determination block 696.

In addition, in this specific example, the cochlear implant 102 comprises an ILD calculation/determination block 695. The ILD calculation block 695 is configured to calculate/determine the ILD for the input signals 589 and 689 received at the hearing aid 150 and cochlear implant 102, respectively. To this end, the ILD calculation block 695 obtains (e.g., receives, determines, etc.) the level ($I_{CI}$) of the input signals 689 received at the cochlear implant and the level ($I_{HA}$) of the input signals 589 received at the hearing aid. The determined ILD, represented by arrow 699, is added to the input signal 689 received at the cochlear implant and provided to an acoustic loudness model 697(B). This provides an estimate of the input signal obtained at the contralateral ear to the ipsilateral ear. This is beneficial if the device on the contralateral ear has insufficient resources to estimate loudness. Alternatively, multiple narrowband ILDs that span the bandwidth of the broadband signal could be calculated at 699 to obtain a more accurate estimate of the signal levels in the individual narrow bands in the contralateral ear. Whereas the acoustic loudness model 697(A) determines the acoustic loudness ($L^I_{CI}$) of the input signals 689 received at the cochlear implant (i.e., the ipsilateral loudness), the acoustic loudness model 697(B) determines the acoustic loudness ($L^I_{HA}$ of the input signals 589 received at the hearing aid 150 (i.e., the contralateral loudness). The acoustic loudness ($L^I_{HA}$) is provided to the target loudness ratio determination block 696.

As shown in FIG. 8, the cochlear implant target loudness ratio ($TLR_{CI}$) is determined by dividing the acoustic loudness ($L^I_{CI}$) of the input signals 689 by the acoustic loudness ($L^I_{HA}$) of the input signals 589. If implemented a hearing aid, the hearing aid target loudness ratio ($TLR_{HA}$) is determined by dividing the acoustic loudness ($L^I_{HA}$) of the input signals 589 by the acoustic loudness ($L^I_{CI}$) of the input signals 689.

It summary FIG. 8 illustrates that, instead of using a loudness model to evaluate the loudness of the input signals on the hearing aid 150 and the cochlear implant 102, the ILD difference could be used to obtain a loudness estimate. In certain embodiments, a simplified version of the acoustic loudness model could be used to save on computations and power because it is the ratio of loudness that is important rather than the actual loudness estimates themselves for this application.

Merely for ease of description, the techniques presented herein have primarily described above with reference to a specific medical device system, namely a bimodal hearing system comprising a cochlear implant and a hearing aid. However, it is to be appreciated that the techniques presented herein may also be used with a variety of other implantable medical device systems. For example, the techniques presented herein may be used with other bimodal hearing systems, including combinations of any of a cochlear implant, middle ear auditory prosthesis (middle ear implant), bone conduction device, direct acoustic stimulator, electro-acoustic prosthesis, auditory brain stimulator systems, etc. The techniques presented herein may also be used with systems that comprise or include tinnitus therapy devices, vestibular devices (e.g., vestibular implants), visual devices (i.e., bionic eyes), sensors, pacemakers, drug delivery systems, defibrillators, functional electrical stimulation devices, catheters, seizure devices (e.g., devices for monitoring and/or treating epileptic events), sleep apnea devices, electroporation devices, etc.

FIG. 9 is a flowchart of a method 900 in accordance with embodiments presented herein. Method 900 begins at 902 where a first hearing prosthesis located at a first ear of a recipient receives a first set of sound signals. The first hearing prosthesis is configured to convert the first set of sound signals into acoustic stimulation signals for delivery to the first ear of the recipient. At 904, a second hearing prosthesis located at a second ear of the recipient receives a second set of sound signals. The second hearing prosthesis is configured to convert the second set of sound signals into electrical stimulation signals for delivery to the second ear of the recipient. At 906, one or more of the first hearing prosthesis or the second hearing prosthesis determines at least one target loudness ratio for the acoustic stimulation signals and the electrical stimulation signals. At 908, one or more of the first hearing prosthesis or the second hearing prosthesis determines at least one inter-aural loudness ratio for the acoustic stimulation signals and the electrical stimulation signals. At 910, one or more of the first hearing prosthesis or the second hearing prosthesis determines one or more adjustments to operation of at least one of the first hearing prosthesis or the second hearing prosthesis so as to match the at least one inter-aural loudness ratio to the at least one target loudness ratio.

It is to be appreciated that the above embodiments are not mutually exclusive and may be combined with one another in various arrangements.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method, comprising:

receiving a first set of sound signals at one or more sound input devices of a first hearing device located at a first ear of a recipient, wherein the first hearing device is configured to convert the first set of sound signals into acoustic stimulation signals for delivery to the first ear of the recipient;

receiving a second set of sound signals at one or more sound input devices of a second hearing device located at a second ear of the recipient, wherein the second hearing device is configured to convert the second set of sound signals into electrical stimulation signals for delivery to the second ear of the recipient;

determining at least one target loudness ratio for the acoustic stimulation signals and the electrical stimulation signals based on the first set of sound signals and the second set of sound signals;

determining at least one inter-aural loudness ratio for the acoustic stimulation signals and the electrical stimulation signals; and matching the at least one inter-aural loudness ratio to the at least one target loudness ratio by adjusting operation of at least one of the first hearing device or the second hearing device.

2. The method of claim 1, wherein the determining the at least one target loudness ratio comprises:

determining an acoustic loudness of the first set of sound signals;

determining an acoustic loudness of the second set of sound signals; and calculating the at least one target loudness ratio based on a ratio of the acoustic loudness of the first set of sound signals and the acoustic loudness of the second set of sound signals.

3. The method of claim 2, wherein determining the acoustic loudness of the second set of sound signals comprises:

determining the acoustic loudness of the second set of sound signals based on an Inter-aural Level Difference (ILD) between the first set of sound signals and the second set of sound signals.

4. The method of claim 1, wherein the determining the at least one inter-aural loudness ratio for the acoustic stimulation signals and the electrical stimulation signals comprises:

determining an estimated acoustic output loudness of the acoustic stimulation signals with an acoustic loudness model;

determining an estimated electric output loudness of the electrical stimulation signals with an electric loudness model; and calculating the at least one inter-aural loudness ratio based on a ratio of the estimated acoustic output loudness and the estimated electric output loudness.

5. The method of claim 1, wherein adjusting operation of at least one of the first hearing device or the second hearing device comprises:

adjusting one or more gain settings at one or more of the first hearing device or the second hearing device.

6. The method of claim 5, wherein adjusting the one or more gain settings at one or more of the first hearing device or the second hearing device comprises:

adjusting at least one broadband gain setting at one or more of the first hearing device or the second hearing device.

7. The method of claim 5, wherein adjusting the one or more gain settings at one or more of the first hearing device or the second hearing device comprises:

adjusting at least one narrowband gain setting adjustment at one or more of the first hearing device or the second hearing device.

8. The method of claim 5, wherein adjusting the one or more gain settings at one or more of the first hearing device or the second hearing device further comprises:

adjusting the one or more gain settings based on a dynamic range of at least one of the first hearing device or the second hearing device.

9. The method of claim 5, wherein adjusting the one or more gain settings at one or more of the first hearing device or the second hearing device further comprises:

adjusting the one or more gain settings based on one or more user inputs.

10. One or more non-transitory computer readable storage media comprising instructions that, when executed by at least one processor, are operable to:

calculate a target loudness ratio of acoustic stimulation signals relative to electrical stimulation signals based on a loudness of input signals received at each of a first hearing device and a second hearing device of a bimodal hearing system;

calculate an instantaneous loudness ratio of acoustic stimulation signals relative to electrical stimulation signals based on a loudness of output signals generated at each of the first hearing device and the second hearing device; and match the instantaneous loudness ratio to the target loudness ratio by adjusting a gain used to generate output signals at either the first hearing device or the second hearing device.

11. The one or more non-transitory computer readable storage media of claim 10, wherein the instructions operable to calculate the target loudness ratio comprise instructions operable to:

determine an acoustic loudness of input signals received at the first hearing device;

determine an acoustic loudness of input signals received at the second hearing device; and calculate the target loudness ratio as a ratio of the acoustic loudness of the input signals received at the first hearing device and the acoustic loudness of the input signals received at the second hearing device.

12. The one or more non-transitory computer readable storage media of claim 11, wherein the instructions operable to determine the acoustic loudness of the input signals received at the second hearing device comprise instructions operable to:

determine the acoustic loudness of the input signals received at the second hearing device based on an Inter-aural Level Difference (ILD) between the input signals received at the first hearing device and the input signals received at the second hearing device.

13. The one or more non-transitory computer readable storage media of claim 10, wherein the instructions operable to calculate the instantaneous loudness ratio comprise instructions operable to:

determine, with an acoustic loudness model, an estimated acoustic output loudness of the output signals generated by the first hearing device;

determine, with an electric loudness model, an estimated electric output loudness of the output signals generated by the second hearing device; and calculate the instantaneous loudness ratio based on a ratio of the estimated acoustic output loudness and the estimated electric output loudness.

14. A first hearing prosthesis configured to operate with a second hearing prosthesis in a bimodal hearing system, the first hearing prosthesis comprising:

one or more sound input devices configured to receive a first set of sound signals; and one or more processors configured to:

convert the first set of sound signals into stimulation signals for delivery to a first ear of a recipient, calculate a target loudness ratio based on a loudness of the first set of sound signals and a loudness of a second set of sound signals received at the second hearing prosthesis, calculate an inter-aural loudness ratio based on a loudness of the stimulation signals for delivery to a first ear of the recipient and a loudness of stimulation signals generated by the second hearing prosthesis for delivery to a second ear of the recipient, and substantially match the inter-aural loudness ratio to the target loudness ratio by adjusting a gain setting for use in generating subsequent stimulation signals for delivery to the first ear of the recipient.

15. The first hearing prosthesis of claim 14, wherein the adjusted gain setting will cause the inter-aural loudness ratio to be within a predetermined range of the target loudness ratio.

16. The first hearing prosthesis of claim 14, wherein to calculate the target loudness ratio, the one or more processors are configured to:

determine an acoustic loudness of the first set of sound signals;

determine an acoustic loudness of the second set of sound signals; and calculate the target loudness ratio based on a ratio of the acoustic loudness of the first set of sound signals and acoustic loudness of the second set of sound signals.

17. The first hearing prosthesis of claim 14, wherein the first hearing prosthesis is a hearing prosthesis configured to deliver one of acoustic stimulation signals or mechanical stimulation signals to the first ear of the recipient, and wherein to calculate the inter-aural loudness ratio, the one or more processors are configured to:

determine, with an acoustic loudness model, an estimated acoustic output loudness of the acoustic stimulation signals or mechanical stimulation signals for delivery to the first ear of the recipient;

determine, with an electric loudness model, an estimated electric output loudness of the stimulation signals for delivery to the second ear of the recipient; and calculate the inter-aural loudness ratio based on a ratio of the estimated acoustic output loudness and the estimated electric output loudness.

18. The first hearing prosthesis of claim 14, wherein the first hearing prosthesis is a hearing prosthesis configured to deliver electrical stimulation signals to the first ear of the recipient, and wherein to calculate the inter-aural loudness ratio, the one or more processors are configured to:

determine, with an electric loudness model, an estimated electric output loudness of the stimulation signals for delivery to the first ear of the recipient;

determine, with an acoustic loudness model, an estimated acoustic output loudness of the stimulation signals for delivery to the second ear of the recipient; and calculate the inter-aural loudness ratio based on a ratio of the estimated acoustic output loudness and the estimated electric output loudness.

* * * * *